Figure 2A:
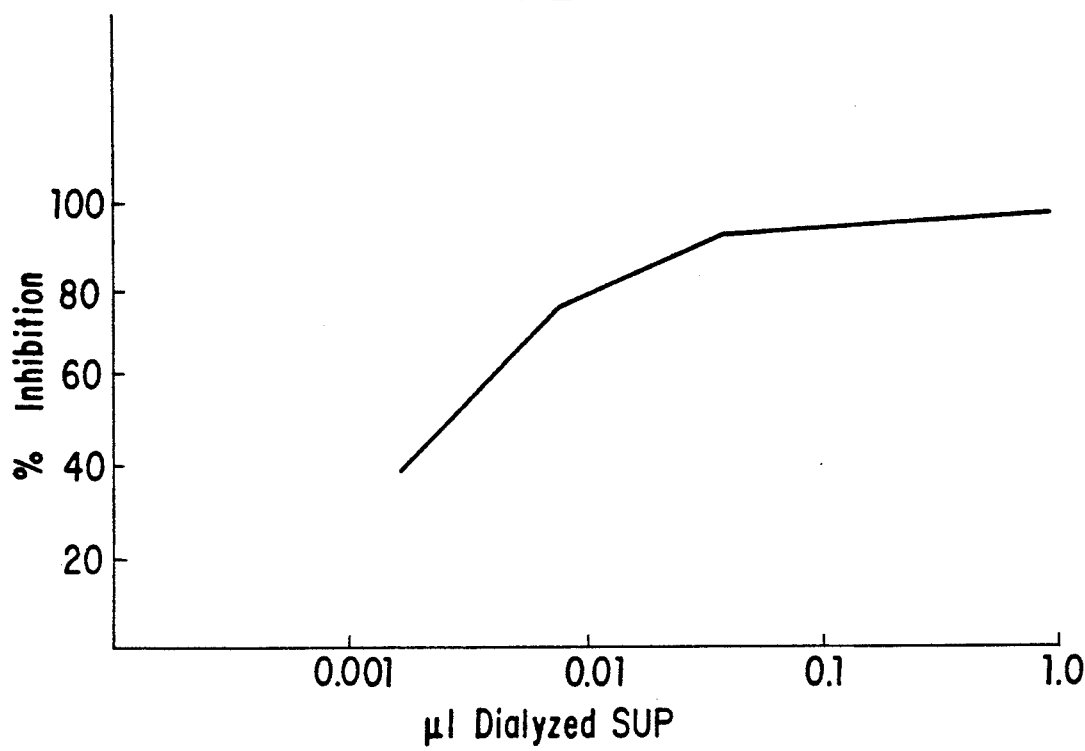

United States Patent [19]

Purchio et al.

[11] Patent Number: 5,304,541
[45] Date of Patent: Apr. 19, 1994

[54] METHODS USING NOVEL CHIMERIC TRANSFORMING GROWTH FACTOR-$\beta 1/\beta 2$

[75] Inventors: Anthony F. Purchio; Linda Madisen, both of Seattle, Wash.; June R. Merwin, Clinton, Conn.

[73] Assignee: Bristol-Myers Squibb Company, New York, N.Y.

[21] Appl. No.: 669,171

[22] Filed: Mar. 14, 1991

Related U.S. Application Data

[63] Continuation-in-part of Ser. No. 667,246, Mar. 8, 1991, Pat. No. 5,244,793, which is a continuation of Ser. No. 284,972, Dec. 15, 1988, abandoned.

[51] Int. Cl.$^5$ .............................................. C07K 13/00
[52] U.S. Cl. ..................................... 514/12; 530/399; 930/120
[58] Field of Search ........................ 530/399; 514/12; 930/120

[56] References Cited

PUBLICATIONS

Gentry et al., *Mol. and Cell Biol.*, 7(10):3418-27 (1987).
Madisen et al., *DNA* 7(1):1-8 (1988).
Meister et al., *J. Gen. Virol.*, 67:1633-1643 (1986).
Keller et al., *J. Exp. Med.*, 168:737-750 (1988).
Postlewaite et al., *J. of Exp. Med.*, 165:251-56 (1987).

*Primary Examiner*—Robert J. Hill, Jr.
*Assistant Examiner*—Shelly Guest Cermak
*Attorney, Agent, or Firm*—Pennie & Edmonds

[57] ABSTRACT

The present invention relates to the production of large quantities of a novel chimeric TGF-$\beta$, termed TGF-$\beta 1/\beta 2$, by eucaryotic host cells transfected with recombinant DNA vectors containing the TGF-$\beta 1/\beta 2$ precursor coding sequence controlled by expression regulatory elements. Simian TGF-$\beta 1$ cDNA (Sharples et al., 1987, DNA 6:239-244) was modified so that the nucleotides encoding amino acid residue numbers 9-13, 17, 19, 25 and 26 of the mature TGF-$\beta 1$ sequence were hanged to the nucleotides encoding the corresponding amino acids of the mature TGF-$\beta 2$ structure. Simian codon usage was maintained. The chimeric TGF-$\beta 1/\beta 2$ of the invention induces effects on the proliferation of vascular endothelial cells equivalent to those induced by TGF-$\beta 1$.

2 Claims, 12 Drawing Sheets

FIG. 1A

```
                Tyr Asn Ser Thr Arg Asp Arg Val Ala Gly Glu Ser Ala Glu Pro Glu
                                                        90                  100
SIMIAN          TAC AAC AGC ACC CGC GAC CGG GTG GCC GGG GAG AGT GCG GAG CCG GAG : 300
HUMAN           ... ... ... ... ... ... ... ... ... ... ... ... ..A ... ..T ... :

Ala Asp Tyr Tyr Ala Lys Glu Val Thr Arg Val Leu Met Val Glu Thr His Asn Glu Ile
                                                        110                                 120
SIMIAN          GCC GAC TAC TAC GCC AAG GAG GTC ACC CGC GTG CTA ATG GTG GAA ACC CAC AAC GAA ATC : 360
HUMAN           ... ... ... ... ... ... ... ... ... ... ... ... ... ... ... ... ... ... ... ... :

Tyr Asp Lys Phe Lys Gln Ser Thr His Ser Ile Tyr Met Phe Phe Asn Thr Ser Glu Leu
                                                        130                                 140
SIMIAN          TAT GAC AAG TTC AAG CAG AGC ACA CAC AGC ATA TAT ATG TTC TTC AAC ACA TCA GAG CTC : 420
HUMAN           ... ... ... ... ... ... ... ... ..T ... ... ... ... ... ... ... ... ... ... ... :

Arg
                Arg Glu Ala Val Pro Glu Pro Val Leu Leu Ser Arg Ala Glu Leu Arg Leu Leu --- Arg
                                                        150
SIMIAN          CGA GAA GCA GTA CCT GAA CCT GTG TTG CTC TCC CGG GCA GAG CTG CGT CTG --- AGG : 477
HUMAN           ... ... ... ..G ... ... ... ... ..C ... ... ... ... ... ... ... ... AGG ... :

Leu Lys Lys Leu Lys Val Glu Gln His Val Glu Gln Lys Tyr Leu Tyr Gln Lys Tyr Ser Asn Asn Ser Trp
                        160                                                     170
SIMIAN          CTC AAG TTA AAA GTG GAG CAG CAT GTG GAG ... TAC CTG TAC CAG AAA TAC AGC AAT AAT TCC TGG : 537
HUMAN           ... ... ... ... ... ... ... ... ..C ... ... ... ... ... ... ... ... ... ... ... :

Asp
                                                                        190
                Arg Tyr Leu Ser Asn Arg Leu Leu Ala Pro Ser Asn Ser Pro Glu Trp Leu Ser Phe Asp
                        180
SIMIAN          CGA TAC CTC AGC AAC CGG CTG CTG GCG CCC AGC AAC TCG CCG GAG TGG TTG TCT TTT GAT : 597
HUMAN           ... ... ... ... ... ... ... ... ... ... ..G ... ... ... ..A ... ... ... ... ... :
```

FIG.1B

| | 200 | | | | | | 210 | | | | | 657 |
|---|---|---|---|---|---|---|---|---|---|---|---|---|
| SIMIAN | Val GTC | Thr ACC | Gly GGA | Val GTT | Val GTG | Arg CGG | Gln CAG | Trp TGG | Leu TTG | Ser AGC | Arg CGC | Gly GGA | Gly GGG | Glu GAA | Ile ATT | Glu GAG | Gly GGC | Phe TTT | Arg CGC | Leu CTT |
| HUMAN | ... | ... | ... | ... | ... | ... | ... | ... | ... | ... | ..T | ... | ... | ... | ... | ... | ... | ... | ... | ... |

| | 220 | | | | | | | 230 | | | | | | | | | | | 717 |
|---|---|---|---|---|---|---|---|---|---|---|---|---|---|---|---|---|---|---|---|---|
| | | | | | | | | | Arg | | | | | | | | | | | |
| SIMIAN | Ser AGC | Ala GCC | His CAC | Cys TGC | Ser TCC | Cys TGT | Asp GAC | Ser AGC | Lys AAA | Asp GAT | Thr ACA | Leu CTG | Gln CAA | Val GTG | Asp GAC | Ile ATC | Asn AAC | Gly GGG | Phe TTC |
| HUMAN | ... | ... | ... | ... | ... | ... | ... | ... | ... | ... | .GG | ... | ... | ... | ... | ... | ... | ... | ... |

| | 240 | | | | | | | 250 | | | | | | | | | | | 777 |
|---|---|---|---|---|---|---|---|---|---|---|---|---|---|---|---|---|---|---|---|---|
| SIMIAN | Thr ACT | Thr ACC | Gly GGC | Arg CGC | Arg CGA | Gly GGT | Asp GAC | Leu CTG | Ala GCC | Thr ACA | Ile ATT | His CAT | Gly GGC | Met ATG | Asn AAC | Arg CGG | Pro CCT | Phe TTC | Leu CTG | Leu CTT |
| HUMAN | ... | ... | ... | ... | ... | ... | ... | ... | ... | ..C | ... | ... | ... | ... | ... | ... | ... | ... | ... | ... |

| | 260 | | | | | | | 270 | | | | | | | | | | | 837 |
|---|---|---|---|---|---|---|---|---|---|---|---|---|---|---|---|---|---|---|---|---|
| SIMIAN | Leu CTC | Met ATG | Ala GCC | Thr ACC | Pro CCA | Leu CTG | Glu GAG | Arg AGG | Ala GCC | Gln CAA | His CAT | Leu CTG | Gln CAA | Ser AGC | Ser TCC | Arg CGG | His CAC | Arg CGC | Arg CGA | Ala GCC |
| HUMAN | ... | ... | ... | ... | ..G | ... | ... | ... | ... | ... | ... | ... | ... | ... | ... | ... | ... | ... | ... | ... |

| | 280 | | | | | | | 290 | | | | | | | | | | | 897 |
|---|---|---|---|---|---|---|---|---|---|---|---|---|---|---|---|---|---|---|---|---|
| SIMIAN | Leu CTG | Asp GAC | Thr ACC | Asn AAC | Tyr TAC | Cys TGC | Phe TTC | Arg AGA | Asn AAT | Val GTG | Gln CAG | Asp GAT | Asn AAT | Cys TGC | Cys TGC | Leu CTA | Arg CGT | Pro CCG | Leu CTT | Tyr TAC |
| HUMAN | ... | ... | ..T | ... | ... | ... | ... | ... | ... | ... | ... | ... | ... | ... | ... | ... | ... | ... | ... | ..C |

| | 300 | | | | | | | 310 | | | | | | | | | | | 957 |
|---|---|---|---|---|---|---|---|---|---|---|---|---|---|---|---|---|---|---|---|---|
| SIMIAN | Ile ATT | Asp GAT | Phe TTC | Lys AAG | Arg AGG | Asp GAT | Leu CTA | Gly GGG | Trp TGG | Lys AAA | Ile ATC | His CAC | Glu GAG | Pro CCC | Lys AAG | Gly GGC | Tyr TAC | His CAT | Ala GCC |
| HUMAN | ... | ... | ... | ... | ... | ... | ... | ... | ... | ... | ... | ... | ... | ... | ... | ... | ... | ... | ... |

FIG.1C

```
              320
              Asn Phe Cys Leu Gly Pro Cys Pro Tyr Ile Trp Ser Leu Asp Thr Gln Tyr Ser Lys Val
SIMIAN        AAC TTC TGC CTG GGG CCC TGT CCC TAC ATT TGG AGC CTG GAC ACG CAG TAC AGC AAG GTC  1017
HUMAN         ... ... ... ... ... ... ..C ... ... ... ... ... ... ... ... ... ... ... ... ...

340                              350
              Leu Ala Leu Tyr Asn Gln His Asn Pro Gly Ala Ser Ala Ala Pro Cys Cys Val Pro Gln
SIMIAN        CTG GCC CTG TAC AAC CAG CAT AAC CCG GGC GCC TCG GCG GCG CCG TGC TGC GTG CCG CAG  1077
HUMAN         ... ... ... ... ... ... ... ... ... ... ... ... ... ... ... ... ... ... ... ...

360                                            370
              Ala Leu Glu Pro Leu Pro Ile Val Tyr Tyr Val Gly Arg Lys Pro Lys Val Glu Gln Leu
SIMIAN        GCG CTG GAG CCA CTG CCC ATC GTG TAC TAC GTG GGC CGC AAG CCC AAG GTG GAG CAG CTG  1137
HUMAN         ... ... ... ..G ... ... ... ... ... ... ... ... ... ... ... ... ... ... ... ...

380                              390
              Ser Asn Met Ile Val Arg Ser Cys Lys Cys Ser
SIMIAN        TCC AAC ATG ATC GTG CGC TCC TGC AAA TGC AGC TGA GGCCCCGCTCCCCCACCCCGGCAG          1204
HUMAN         ... ... ... ... ... ... ... ..G ... ... ... ... ..........................G......

SIMIAN        GCCCGGCCCCGCCCCACCCCCGTCTTGCCCTTGGGGGCTGTGTATTTAAGGACACCCGTGCCCAAGCCCACC            1283
HUMAN         ........A.....G..........C.....A......................T..................

SIMIAN        TGGGGCCCCATTAAAGA                                                                 1300
HUMAN         .................
```

METHODS USING NOVEL CHIMERIC TRANSFORMING GROWTH FACTOR-β1/β2

This application is a CIP of 07/667,246, filed Mar. 8, 1991, now U.S. Pat. No. 5,244,793, which is a continuation of 07/284,972 filed Dec. 15, 1988, now abandoned.

TABLE OF CONTENTS

1. Introduction
2. Background of the Invention
  2.1. Intracellular Processing of TGF-β1
3. Summary of the Invention
4. Description of the Figures
5. Detailed Description of the Invention
  5.1. Generation of the Chimeric TGF-β1/β2 Coding Sequence
  5.2. Construction of Expression Vectors Containing the Chimeric TGF-β1/β2 Coding Sequence
  5.3. Identification of Transfectants Expressing Chimeric TGF-β1/β2
  5.4. Improved Method for Producing Mature TGF-β1/β2
6. Example: Production of TGF-β1/β2 by Expression in Chinese Hamster Ovary Cells
  6.1. Materials and Methods
  6.1.1. DNA Transfections
  6.1.2. Selection of Methotrexate Resistant Cells
  6.1.3. Growth Inhibition Assay
  6.1.4. Peptide Synthesis and Production of Antibodies
  6.1.5. Immunoblotting
  6.1.6. Construction of Plasmid Programing the Synthesis of TGF-β1/β2
  6.2 Expression of TGF-β1/β2 in CHO Cells
7. Example: Growth Modulation of Vascular Endoethelial Cells by Hybrid TGF-5β
  7.1. Material and Methods
  7.1.1. Cell Culture
  7.1.2. TGF-β Factors
  7.1.3. Matrix Components
  7.1.4. Proliferation Inhibition Assay
  7.1.5. Cell Migration Assays
  7.2 Results
8. Deposit of Microorganisms

1. INTRODUCTION

The present invention relates to a novel chimeric transforming growth factor-beta termed TGF-β1/β2 (or TGF-5β), to nucleotide sequences (SEQ ID No. 1) and expression vectors encoding TGF-β1/β2, and to methods for the production of TGF-β1/β2. The invention is exemplified by the production and secretion of TGF-β1/β2 by CHO cells transfected with expression vectors encoding a chimeric TGF-β1/β2 precursor gene (SEQ ID No. 1). The chimeric gene product possesses TGF-β biological activity.

2. BACKGROUND OF THE INVENTION

Transforming growth factor-Beta (TGF-β) is a member of a recently described family of polypeptides that regulate cellular differentiation and proliferation. Other members of this family include Müllerian inhibitory substance (Cate et al., 1986, Cell 45:685-698), the inhibins (Mason et 1985, Nature 318:659-663) and a protein predicted from a transcript of the decapentaplegic gene complex of Drosophila (Padgett et al., 1987, Nature 325:81-84).

Four types of TGF-β have been identified and designated TGF-β1, TGF-β2, TGF-β1.2, and TGF-β3. The first described type, TGF-β1, consists of two identical disulfide linked subunits having molecular weights of 13,000 (Assoian et al., 1983, J. Biol. Chem. 258:7155-7160; Frolik et al, 1983, Proc. Natl. Acad. Sci. USA 80:3676-3680; Frolik et al., 1984, J. Biol. Chem. 260:10995-11000). It has been purified from several tissue sources including placenta (Frolik et al., 1983, Nature 325:81-84), blood platelets (Childs et al., 1982, Proc. Natl. Acad. Sci. USA 79:5312-5316; Assoian et al., 1983, J. Biol. Chem. 258:7155-7160) kidney (Roberts et al., 1983, Biochemistry 22:5692-5698), and demineralized bone (Seyedin et al., 1985, Proc. Natl. Acad. Sci. USA 82:119-123). cDNA clones coding for human (Derynck et al., 1985, Nature 316:701-705), mouse (Derynck et al., 1986, J. Biol. Chem. 261:4377-4379) and simian (Sharples et al., 1987, DNA 6:239-244) TGF-β1 have been isolated. DNA sequence analysis of these clones indicates that TGF-β1 is synthesized as a large precursor polypeptide, the carboxy terminus of which is cleaved to yield the mature TGF-β monomer. Strong sequence homology has been found throughout the TGF-β1 precursor protein from all of the above sources.

In the presence of 10% serum and epidermal growth factor, TGF-β1 promotes the anchorage independent growth of normal rat kidney fibroblasts (Roberts et al., 1981, Proc. Natl. Acad. Sci. USA 78:5339-5343; Roberts et al., 1982, Nature 295:417-419; Twardzik et al., 1985, J. Cell. Biochem. 28:289-297); in the presence of 10% serum alone, it is able to induce colony formation of AKR-2B fibroblasts (Tucker et al., 1983, Cancer Res. 43:1518-1586). TGF-β1 has also been shown to cause fetal rat muscle mesenchymal cells to differentiate and produce cartilage specific macromolecules (Seyedin et al., 1986, J. Biol. Chem. 261:5693-5695).

In contrast to its effect on cell proliferation, TGF-β1 purified from human platelets has been shown to inhibit the growth of certain cells in culture (Tucker et al., 1984, Science 226:705-707). TGF-β1 has also been shown to inhibit the growth of several human cancer cell lines (Roberts et al., 1985, Proc. Natl. Acad. Sci. USA 82:119-123). This inhibitory/stimulatory effect of TGF-β1 may depend on several factors including cell type and the physiological state of the cells (for review see Sporn et al., 1986, Science 233:532-534).

TGF-β2, like TGF-β1, is a polypeptide of molecular weight 26,000 composed of two identical 13,000-dalton subunits which are disulfide linked (Chiefetz et al., 1987, Cell 48:409-415; Ikeda et al., 1987, Biochemistry 26:2406-2410) and has been isolated from bovine demineralized bone (Seydin et al., 1987, J. Biol. Chem. 262:1946-1949), porcine platelets (Cheifetz et al., 1987, 48:409-415), a human prostatic adenocarcinoma cell line, PC-3 (Ikeda et al., 1987, Biochemistry 26:2406-2410), and a human glioblastoma cell line (Wrann et al., 1987, EMBO 6:1633-1636). cDNA clones coding for human and simian TGF-β2 have been isolated (Madisen et al., 1988, DNA 7:1-8; Webb et al., 1988, DNA 7:493-497). The mature TGF-β2 monomer is cleaved from one of two larger precursor polypeptides, the mRNAs of which may arise via differential splicing (Webb et al., 1988, DNA 7:493-497).

TGF-β1 and TGF-β2 share 71% amino acid sequence identity in their mature regions, and 41% identity in their precursor structures. TGF-β3, the amino acid sequence of which has very recently been deduced from cDNA clones, appears to contain a C-terminal 112 amino acid sequence with about 80% homology to the mature monomers of TGF-$\beta$1 and TGF-$\beta$2 (Dijke et al., 1988, Proc. Natl. Acad. Sci. USA 85:4715–4719). TGF-$\beta$1.2 is a heterodimeric form comprising a $\beta$1 and $\beta$2 subunit linked by disulfide bonds (Cheifetz et al., 1987, Cell 48:409–415).

2.1. INTRACELLULAR PROCESSING OF TGF-$\beta$1

The amino portion of the precursor region of TGF-$\beta$1 from human, rodent and simian sources show a high degree of homology (Derynck et al., 1985, Nature 316:701–705; Derynck et al., 1986, J. Biol. Chem. 261:4377–4379; Sharples et al., 1987, DNA 6:239–244), suggesting an important biological function may be associated with this part of the molecule. Recent studies demonstrating that this portion of the TGF-$\beta$1 precursor is glycosylated and phosphorylated support this contention since one might assume that a cell would not go through the expense of performing these secondary modifications were it not for a specific function (Brunner at al., 1988, Mol. Cell. Biol. 8:2229–2232). These modifications may be important for dimerization of the precursor or for directing its movement out of the cell. There is evidence which suggests that glycosylation of the precursor is involved in the transport of mature TGF-$\beta$1 out of the cell (Purchio et al., 1988, J. Biol. Chem. 263:14211–4215).

The existence of what may either be intermediate precursor complexes involved in processing or expression artifacts in CHO cells expressing the simian TGF-$\beta$1 gene has been reported (Gentry et al., 1988, Mol. Cell. Biol. 8:4162-168 press; Gentry et al., 1987, Mol. Cell. Biol. 7:3418–427). These studies revealed that the TGF-$\beta$1 precursor synthesized by transfected CHO cells consists of pro-TGF-$\beta$1, mature TGF-$\beta$1, and the pro region of the precursor interlinked by disulfide bonds. Such disulfide-linked precursor complexes have also been observed in isolated latent forms of TGF-$\beta$1 (Miyazano et al., 1988, J. Cell. Biochem. Suppl. 12(A):200; Wakefield et al., 1987, J. Biol. Chem. Suppl. 11(A):46).

Gentry et al. (Gentry et al., 1988, Mol. Cell. Biol., 8:4162–4168) have proposed the following scheme for the processing of pre-pro-TGF-$\beta$1 in transfected CHO cells. (The amino acid position numbers referred to are from the published sequence of simian TGF-$\beta$1 (Sharples et al., 1987, DNA 6:239–244)). According to this proposed scheme, the first step involves signal peptide cleavage at the Gly-29/Leu-30 peptide bond. This cleavage event most likely occurs co-translationally during transit of the precursor through the rough endoplasmic reticulum membrane (Blobel and Dobberstein, 1975, J. Cell. Biol. 67:835–851; Walter et al., 1984, Cell 38:5–8). Following cleavage of the signal peptide, core glycosylation units (Rothman et al., 1978, Cell 15:1447–1454) are added to pro-TGF-$\beta$1 at each of three predicted N-glycosylation sites located at Asn-82, Asn-136 and Asn-176. The core glycosylated pro-TGF-$\beta$1 is then sequentially processed during transit through the Golgi to yield a phosphorylated glycoprotein containing complex, sialated oligosaccharides. At some stage during synthesis or transit, proteolytic cleavage at the dibasic residue and disulfide isomerization occurs, releasing mature TGF-$\beta$1.

In another recent study, mannose-6-phosphate was identified in the TGF-$\beta$1 precursor. Mannose-6-phosphate, a phosphorylated sugar analog, appears to play a fundamental role in the targeted transport and intercellular exchange of lysosomal enzymes (von Figura, 1986, Ann. Rev. Biochem. 55:167-193). Specific receptors which recognize the mannose-6-phosphate residues of lysosomal enzymes have been identified and are essential components of the transport system. Secreted lysosomal proteins containing mannose-6-phosphate have been identified in the conditioned medium of tissue culture cells (Gal and Gottesman, 1986, J. Biol. Chem. 261:1760–1765; Capony et al., 1981, J. Cell. Biol. 104:253–262; Baumbach et al., 1984, Proc. Natl. Acad. Sci. USA 1:2985-2989; Sahagian and Gottesman, 1982, J. Biol. Chem. 57:11145–11150). It is possible that the mannose-6-phosphate residues of the TGF-$\beta$1 precursor may direct pro-TGF-$\beta$1 to lysosomes for proteolytic processing to yield mature TGF-$\beta$1. Alternatively, the mannose-6-phosphate residues may function to target the cleaved TGF-$\beta$1 precursor to lysosomes for degradation.

3. SUMMARY OF THE INVENTION

The present invention relates to the production of large quantities of a novel chimeric TGF-$\beta$, termed TGF-$\beta$1/$\beta$2, by eucaryotic host cells transfected with recombinant DNA vectors containing the TGF-$\beta$1/$\beta$2 precursor coding sequence (SEQ ID No. 1) controlled by expression regulatory elements. Simian TGF-$\beta$1 cDNA (Sharples et al., 1987, DNA 6:239–244) was modified so that the nucleotides encoding amino acid residue numbers 9–13, 17, 19, 25 and 26 of the mature TGF-$\beta$1 sequence were changed to the nucleotides encoding the corresponding amino acids of the mature TGF-$\beta$2 structure. Simian codon usage was maintained.

Expression vectors encoding the chimeric TGF-$\beta$1/$\beta$2 precursor under the regulatory control of Simian Virus 40 (SV 40) expression regulatory elements were constructed and used to transfect Chinese Hamster ovary (CHO) cells. CHO transfectants which synthesize and secrete high levels of mature TGF-$\beta$1/$\beta$2 were obtained. TGF-$\beta$1/$\beta$2 expression was amplified with methotrexate and amplified transfectants secreted as much as 1 mg/L mature TGF-$\beta$1/$\beta$2. Acidification of the conditioned media of the CHO transfectants resulted in maximal levels of bioactive TGF-$\beta$1/$\beta$2. It is believed that the high levels of mature TGF-$\beta$1/$\beta$2 secreted by the transfected CHO cells results from an unusual efficiency in the proteolytic processing of the chimeric precursor protein. Such increased processing efficiency may, in turn, result from structural characteristics affected by applicants' combination of the TGF-$\beta$1 and TGF-$\beta$2 amino acid sequences in the amino-terminal domain of the mature TGF-$\beta$ structure.

The chimeric TGF-$\beta$1/$\beta$2 of the invention induces effects on the proliferation of vascular endothelial cells equivalent to those induced by TGF-$\beta$1 (see Section 7., et seq.).

4. DESCRIPTION OF THE FIGURES

Figure 1A:
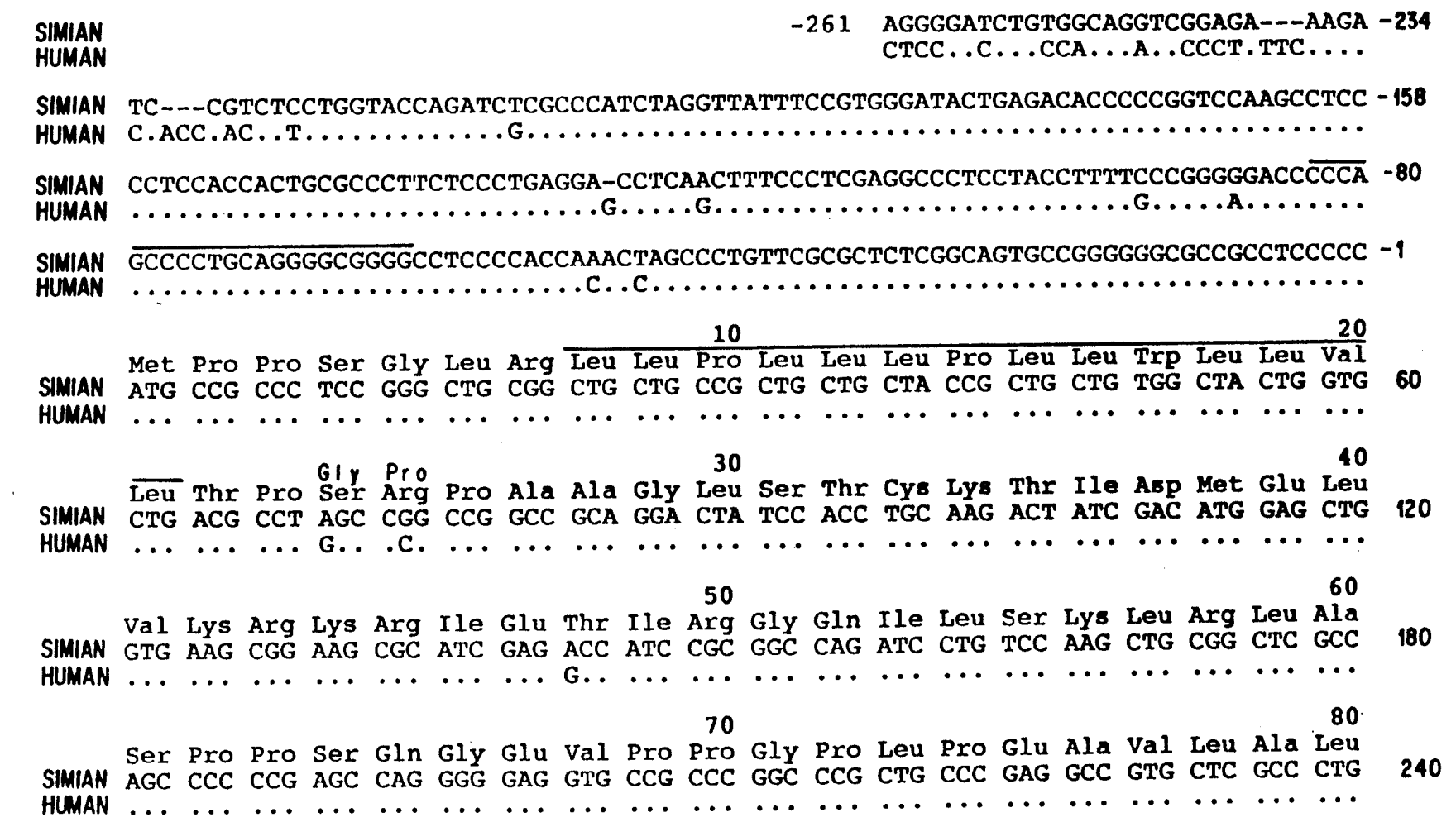

FIG. 1. Nucleotide and deduced amino acid sequence (SEQ ID No.: 1,2) of the TGF-$\beta$1/$\beta$2 hybrid protein encoded by expression plasmid p5/dhfr.

Figure 2B:
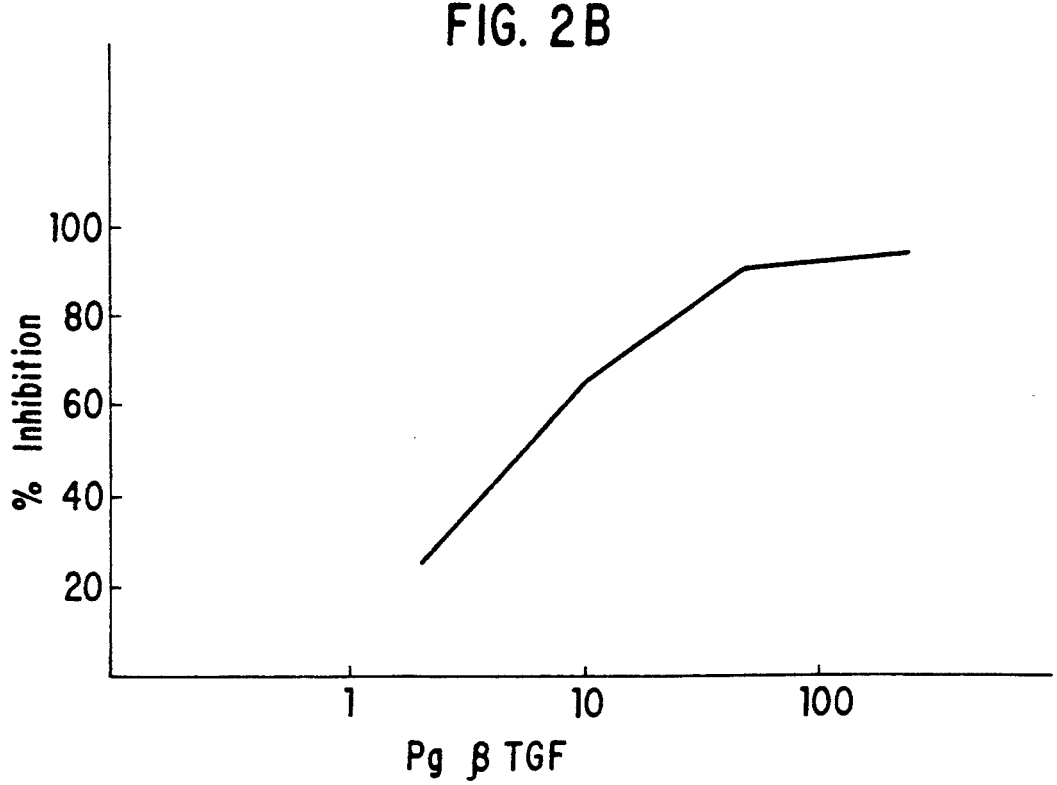

FIG. 2A–2B Bioactivity of conditioned media from 5$\beta$41,2.5 cells. Bioactivity was measured by the growth inhibition assay of CCL-64 mink lung epithelial cells. 2(A) Serum-free media conditioned by 5$\beta$41,2.5 cells for 24 hours was dialyzed against 0.2 M acetic acid and assayed as described in Section 6.1.3., infra. 2(B) Standard growth inhibition curve for TGF-β1.

Figure 3:
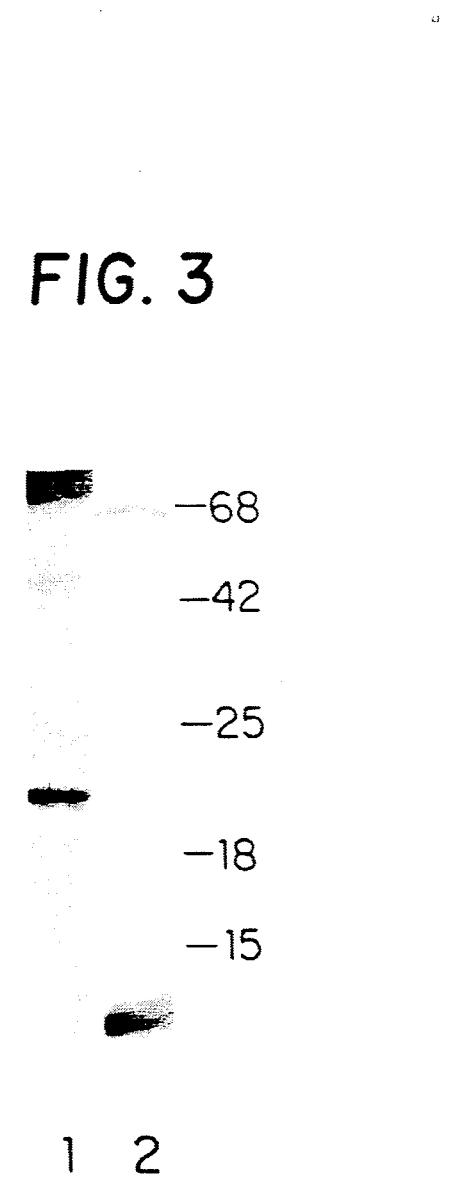

FIG. 3. Immunoblot analysis of proteins secreted by 5β41,2.5 cells. 5β41,2.5 cells were grown to confluence; media was dialyzed against 0.2 M acetic acid and assayed by immunoblotting under nonreducing (lane 1) or reducing (lane 2) conditions with anti-TGF-β1$_{369-381}$ as described in Section 6.1.5., infra.

Figure 4A:
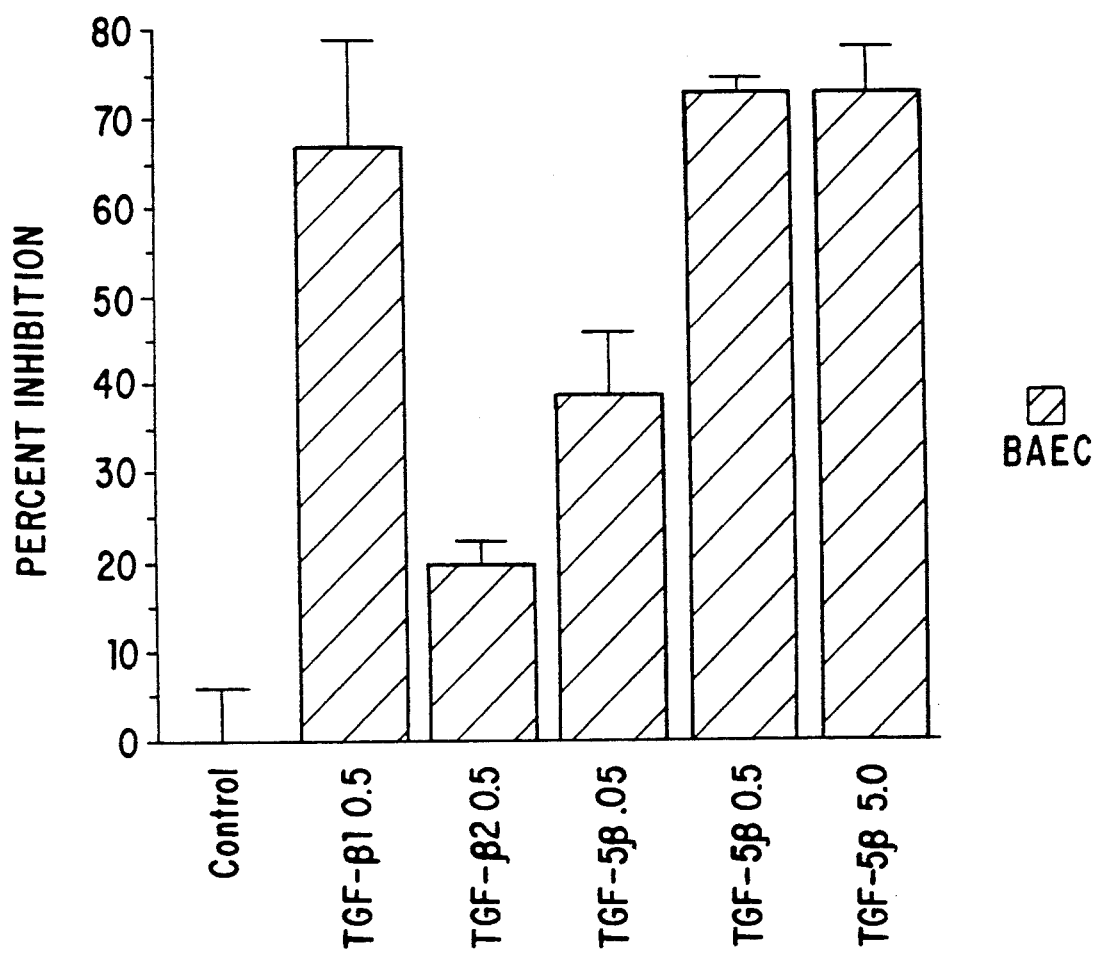
Figure 4B:
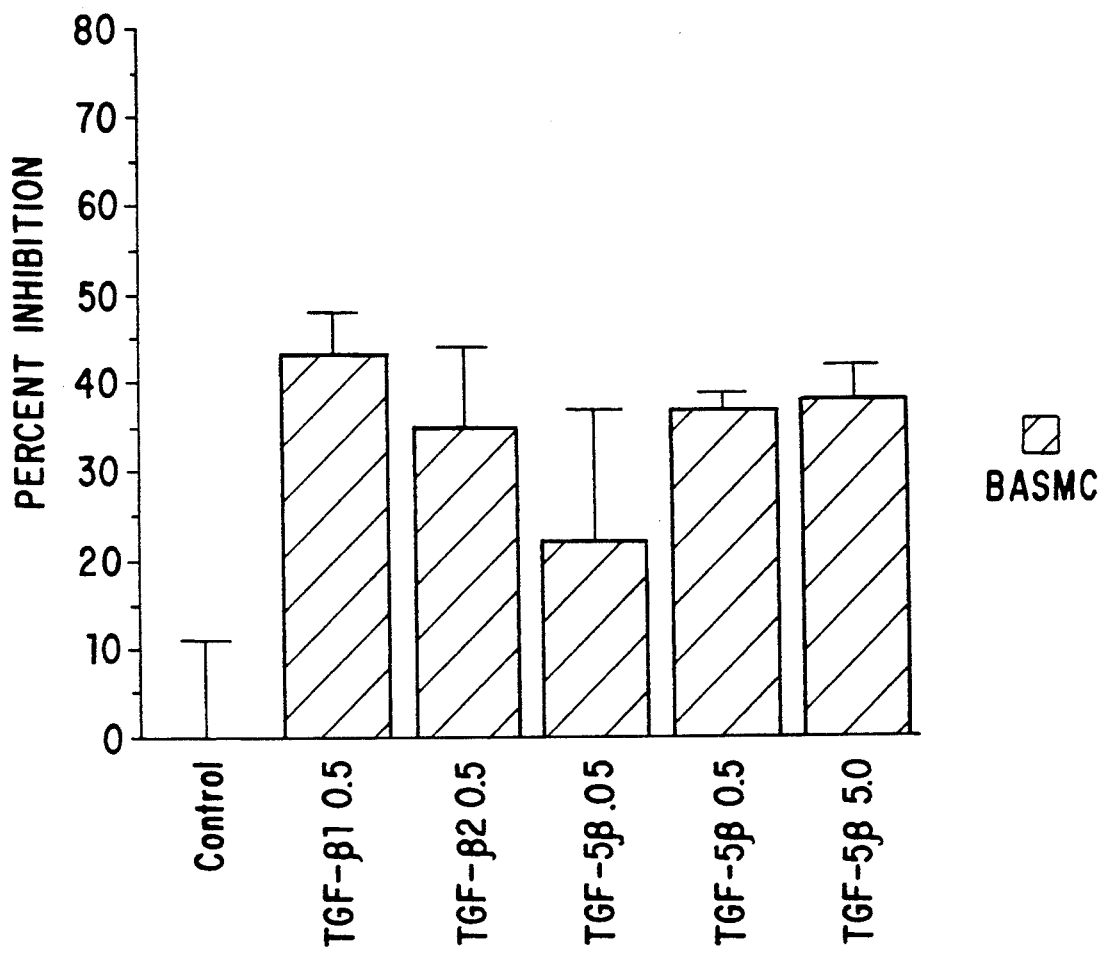
Figure 4C:
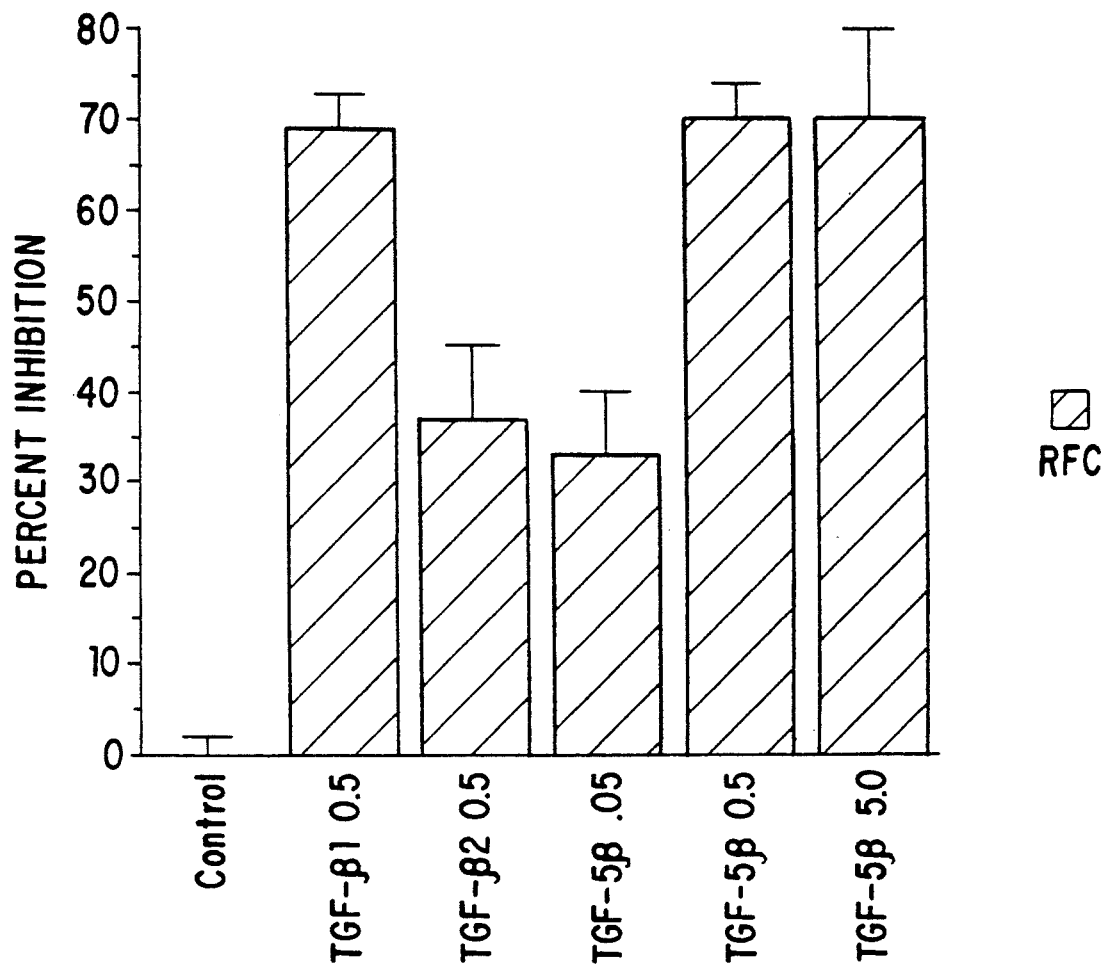

FIG. 4A–4C. Effect of various TGF-βs on vascular endothelial cells. Two-dimensional, five-day vascular cell cultures were grown in DME plus 10% FCS (control) with additions of TGF-β1, TGF-β2, both at 0.5 ng/ml, or TGF-5 at concentrations of 0.05, 0.5 or 5.0 ng/ml. 4(A) BAEC;4(B) BASMC;4(C) RFC. In all cases the TGF-5β hybrid molecule mimicked the TGF-β1 isoform.

Figure 5:
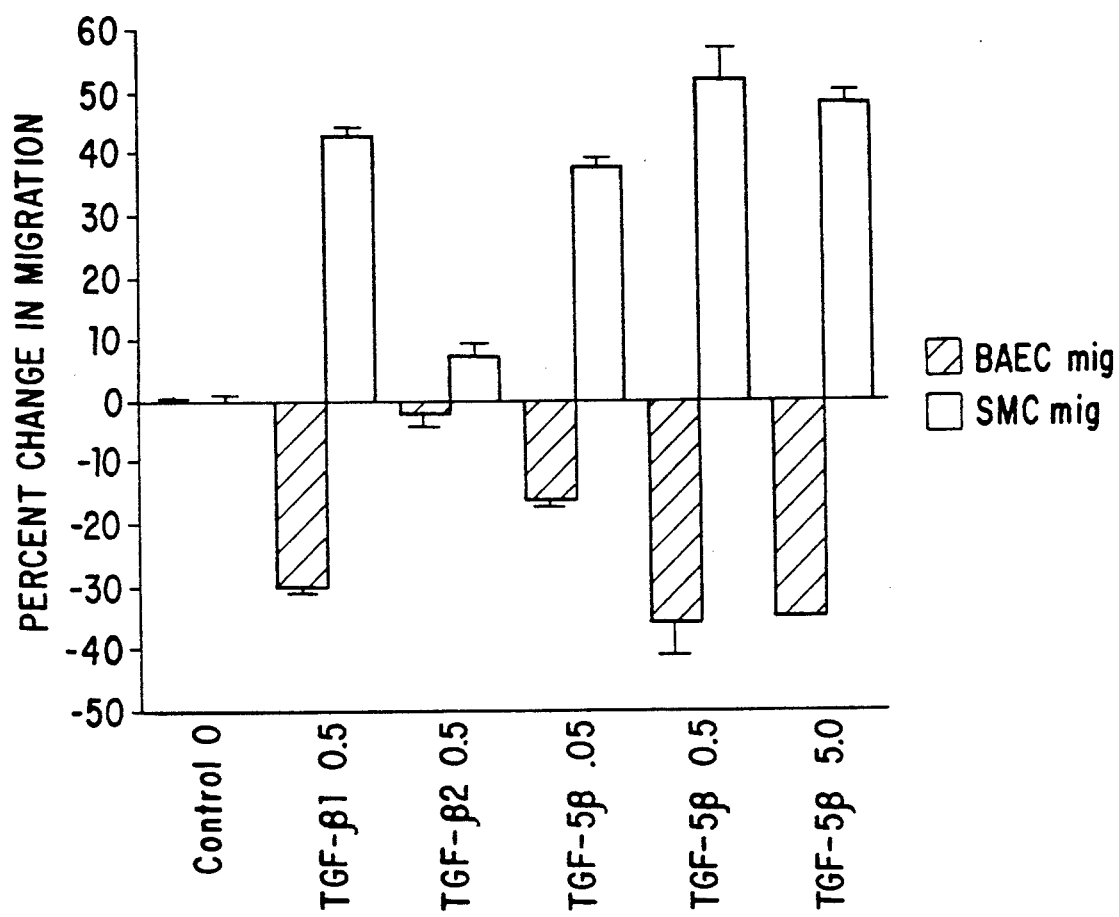

FIG. 5. Effect of various TGF-βs on vascular cell migration. Migrating aortic endothelial and smooth muscle cells were treated with TGF-β1 and TGF-β2 at 0.5 ng/ml and TGF5β at concentrations of 0.05, 0.5 or 5.0 ng/ml. TGF-5β mimicked the TGF-β1 response induced on BASMCs by increasing migratory rates, while the opposite effect was seen when using large vessel endothlial cells. TGF-β2 elicited no effect on either cell type.

FIG. 6A–6F. Angiogenic response induced by various TGF-βs. Three-dimensional RFC cultures were viewed with Hoffman interference microscopy to analyze angiogenic responses elicited by TGF-β1, TGF-β2, and TGF-5β. Four-day, 3-D small vessel endothelial cultures were cryosectioned at 8 μm and acetone fixed. Control cultures 6(A) were grown in DME plus 10% FCS. Treated cultures included: 6(B) TGF-β1 (0.5 ng/ml); 6(C) TGF-β2 (0.5 ng/ml); and TGF-5β at 6(D) 0.05 ng/ml; 6(E) 0.5 ng/ml and(F) 5.0 ng/ml. TGF-β1 evokes complex, branching tubular structures, while the control cultures showed minimal tube formation. TGF-5β at 0.05 ng/ml gave an indication of commencing neovascularization, while 0.5 ng/ml of the hybrid molecule stimulated an angiogenic response equivalent to the TGF-β1 isoform. The highest concentration of TGF-5β appears to cause a slight decrease in the amount of complex branching structures which had been shown before using TGF-β1. TGF-β2 required a 10-fold increase in concentration (5.0 ng/ml) in order to match the neovasularization induced by TGF-β1 and TGF-5β at 0.5 ng/ml. Arrows indicate tubular formations by RFCs. Magnification = 100 X.

5. DETAILED DESCRIPTION OF THE INVENTION

The present invention relates to TGF-β1/β2, to nucleotide sequences (SEQ ID No.: 1) encoding TGF-β1/β2 and the TGF-β1/β2 precursor, and to the production of TGF-β1/β2 by recombinant DNA methods. TGF-β1/β2, a novel chimeric transforming growth factor-beta, is biologically active in the standard assay used to measure TGF-β1 bioactivity and is immunoreactive with TGF-β1-specific antibodies. A chimera structurally comprising a combination of TGF-β1 and TGF-β2 amino acid sequences (SEQ ID No.: 2), the TGF-β1/β2 of the invention is likely to carry a novel portfolio of biological activities, some of which may be similar or nearly identical to those exhibited by its parent molecules while others may be unique to TGF-β1/β2. With regard to those bioactivities which are similar or nearly identical to those of TGF-β1 or TGF-β2, this new factor may provide a more effective means of inducing corresponding biological responses and its use may therefore be a desirable alternative to TGF-β1 and TGF-β2 in various medical applications envisioned for the TGF-βs. Such applications include but are not limited to inducing or accelerating cell proliferation and differentiation and, inhibiting cell division. Thus TGF-β1/β2 may find uses in, for example, treating cancer and promoting wound healing.

The method of the invention may be divided into the following stages solely for the purposes of description: (a) generation of the coding sequence (SEQ ID No. 1) for the TGF-β1/β2 precursor; (b) construction of an expression vector which will direct the expression of the TGF-β1/β2 coding sequence (SEQ ID No. 1); (c) transfection of appropriate host cells which are capable of replicating, expressing the gene and processing the gene product to produce the mature form of TGF-β1/β2 and/or TGF-β1/β2 precursors; and (d) identification and purification of the TGF-β1/β2 precursors and the mature, biologically active TGF-β1/β2.

Once a transfectant is identified that expresses high levels of TGF-β1/β2 precursors and/or mature TGF-β1/β2, the practice of the method of the invention involves the expansion of that clone and isolation of the gene product expressed.

The method of the invention is demonstrated herein, by way of examples in which simian TGF-β1 precursor cDNA (Sharples et al., 1987, DNA 6:239–244) is modified so that the nucleotides encoding amino acid residue numbers 9–13, 17, 19, 25 and 26 of the mature simian TGF-β1 sequence are changed to the nucleotides encoding the corresponding amino acids in the mature TGF-β2 structure, while maintaining simian codon usage. The resulting chimeric TGF-β1/β2 precursor coding sequence (SEQ ID No. 1) is then used to construct expression vectors which are capable of directing the synthesis of the mature TGF-β1/β2 product.

The effects of TGF-β1/β2 on the proliferation, migration and angiogensis of vascular endothelial cells have been examined in vitro (section 7., et seq.) and appear to closely parallel those induced by TGF-β1 but not TGF-β2.

The various aspects of the method of the invention are described in more detail in the subsections below and in the examples that follow.

5.1. GENERATION OF THE CHIMERIC TGF-β1/β2 CODING SEQUENCE

The nucleotide coding sequence (SEQ ID No.: 1) for the chimeric TGF-β1/β2 is depicted in FIG. 1. In the practice of the method of the invention, this nucleotide sequence (SEQ ID No.: 1) or its functional equivalent can be used to generate the recombinant molecules which will direct the expression of the TGF-β1/β2 product. Due to the degeneracy of the nucleotide coding sequences, other DNA sequences as depicted in FIG. 1 may be used in the practice of the present ion. Such alterations of the nucleotide sequence (SEQ ID No.: 1) of FIG. 1 include deletions, additions or substitutions of different nucleotide residues resulting in a sequence that encodes the same or a functionally equivalent gene product. The gene product may contain deletions, additions or substitutions of amino acid residues within a sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharge dpolar head groups or nonpolar head groups having similar hydrophilicity values include the following: leucine, isoleucine, valine; glycine, alanine; asparagine, glutamine; serine, threonine; phenylalanine, tyrosine.

The nucleotide sequence for simian TGF-$\beta$1 may be obtained from simian cell sources (Sharples et al., 1989, DNA 6:239-244). Te nucleotide sequence of the chimeric TGF-$\beta$1/$\beta$2 in FIG. 1 (SEQ ID No. 1) may be prepared by methods known in the art including but not limited to the use of DNA restriction enzymes, synthetic oligonucleotides, and DNA ligases. Alternatively, the coding sequence of FIG. 1 (SEQ ID No.: 1) may be synthesized in whole or in part using chemical methods well known in the art.

In a specific embodiment of the invention, the coding sequence for simian TGF-β1 was obtained from a full length cDNA clone obtained from an African green monkey cell line, BSC-40 (Sharples et al., 1987, supra). The coding sequence of chimeric TGF-β1/β2 depicted in FIG. 1 (SEQ ID No. 1) was then derived from the simian TGF-β1 cDNA by removing and replacing the coding sequences of amino acid residue numbers 9, 10, 11, 12, 13, 17, 19, 25 and 26 of the mature TGF-β1 molecule with the coding sequences for amino acid residue numbers 9, 10, 11, 12, 13, 17, 19, 25 and 26 of the mature TGF-β2 molecule (Madisen et al., 1988, DNA 7:1-8) using gene construction techniques.

5.2. CONSTRUCTION OF EXPRESSION VECTORS CONTAINING THE CHIMERIC TGF-β1/β2 CODING SEQUENCE

In order to express biologically active, mature TGF-β1/β2, an expression vector/host system should be chosen which provides not only for high levels of transcription and translation but for the correct processing of the gene product. This is especially important when employing the entire coding sequence (SEQ ID No.: 1) of the chimeric TGF-β1/β2 precursor in the expression constructs because, like TGF-β1 and TGF-β2, the mature chimeric TGF-β1/β2 is believed to be released from a precursor molecule or complex of molecules via cellular processing events. In addition, an expression/host cell system which provides for secretion of the product may be desirable.

In particular, it appears that mature TGF-β1/β2 is a disulfide linked homodimer of 112 amino acids per subunit formed by cellular processing events believed to be similar to those which form mature TGF-β1 and TGF-β2. The TGF-β1/β2 precursor has three potentional N-glycosylation sites in its pro domain (Sharples et al., 1987, DNA 6:239-244). Studies involving TGF-β1 have determined that N-glycosylation and phosphorylation in the pro domain of TGF-β1 occurs in transfected CHO cells, implicating an important functional role for the precursor in the cellular synthesis and release or seretion of the mature molecule (Brunner et al., 1988, Mol. Cell. Biol. 8:2229-2232). The presence of mannose-6-phosphate in the TGF-β1 precursor also supports the hypothesis that the precursor has independent functional activity (Purchio et al., 1988, J. Biol. Chem. 263:14211-14215). Since the chimeric TGF-β1/β2 precursor contains the simian TGF-β1 pro domain, applicants believe it likely that the TGF-β1/β2 precursor is functionally active and important to the correct processing the mature TGF-β1/β2 molecule. Thus, the ability of a host cell used in the expression system to correctly express and process chimeric TGF-β1/β2 is important to the production of a mature, bioactive product.

In a specific embodiment described herein, mature bioactive TGF-β1/β2 is successfully produced using simian virus 40 (SV40) expression control elements in a Chinese Hamster Ovary (CHO) host cell system. However, a variety of other animal host/expression vector systems (i.e., vectors which contain the necessary elements for directing the replication, and translation of the TGF-β1/β2 coding sequence (SEQ ID No.: 1) in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionein promoter).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionein promoter) or from viruses that grow in these cells, (e.g. vaccinia virus 7.5K promoter) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. For example, in cases where only a portion of the TGF-β1/β2 coding sequence (SEQ ID No.: 1) is inserted, exogenous translational control signals, including the ATG initiation codon must be provided. Furthermore, the initiation codon must be in phase with the reading frame of the TGF-β1/β2 coding sequences (SEQ ID No.: 1) to ensure translation of the entire insert. These exogenous translational control signals and initiation codons can be of a variety of origins, both natural and synthetic. The efficiency of expression may be enhanced by the inclusion of transcription attenuation sequences, enhancer elements, and the like.

Any of the methods previously described for the insertion of DNA fragments into a vector may be used to construct expression vectors containing the TGF-β1/β2 coding sequence (SEQ ID No.: 1) and appropriate transcriptional/translational control signals. These methods may include in vitro recombinant DNA techniques, synthetic techniques and in vivo recombinations (genetic recombination).

In cases where an adenovirus is used as an expression vector, the TGF-β1/β2 coding sequence (SEQ ID No.: 1) may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing chimeric TGF-β1/β2 in infected hosts. Similarly, the vaccinia 7.5K promoter may be used.

An alternative expression system which could be used to express TGF-β1/β2 is an insect system. In one such system, *Autographa californica* nuclear polyhedrosis virus (AcNPV) is used as a vector to express foreign genes. The virus grows in *Sodoptera frugiperda cells*. The TGF-β1/β2 coding sequence (SEQ ID No.: 1) may be cloned into non-essential regions example, the polyhedrin gene) of the virus and placed under the control of an AcNPV promoter (for example, the polyhedrin promoter). Successful insertion of the TGF-β1/β2 coding sequence (SEQ ID No.: 1) will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed.

In addition, a host cell strain may be chosen which modulates the expression of the inserted sequences, or modifies and processes the gene product in the specific fashion desired. Expression from certain promoters can be elevated in the presence of certain inducers, (e.g. zinc and cadmium ions for metallothionein promoters). Therefore, expression of the genetically engineered TGF-β1/β2 may be controlled. This is important if the protein product of the cloned foreign gene is lethal to host cells. Furthermore, post-translational modifications such as glycosylation, and processing events such as proteolytic cleavage of protein products, may be important to the functionality of the protein. Different host cells have characteristic and specific mechanisms for the post-translational processing and modification of proteins. Appropriate cell lines or host systems can be chosen to ensure the correct modification and processing of the foreign protein expressed.

In a specific embodiment of the invention, an expression vector containing the TGF-β1/β2 coding sequence (SEQ ID No. 1) in tandem with the mouse dihydrofolate reductase gene (dhfr) under the control of SV40 regulatory sequences is constructed and used to transfect dhfr-deficient CHO cells. CHO transfectants expressing the dhfr phenotype are isolated by propagation in selective media. To increase the level of expression of TGF-β1/β2, transfectants may be exposed to increasing concentrations of methotrexate in order to isolate clones transcribing amplified levels of TGF-β1/β2 mRNA. TGF-β1/β2 mRNA levels may be assayed at various stages of amplification by solution hybridization (Uhler et al., 1986, Proc. Natl. Acad. Sci. U.S.A. 83:1300–1304).

5.3. IDENTIFICATION OF TRANSFECTANTS EXPRESSING CHIMERIC TGF-β1/β2

The host cells which contain the TGF-β1/β2 coding sequence (SEQ ID No. 1) and which express the biologically active, mature product may be identified by at least four general approaches: (a) DNA-DNA hybridization; (b) the presence or absence of "marker" gene functions; (c) assessing the level of transcription as measured by the expression of TGF-β1/β2 mRNA transcripts in the host cell; and (d) detection of the mature gene product as measured by immunoassay and, ultimately, by its biological activities.

In the first approach, the presence of the TGF-β1/β2 coding sequence (SEQ ID No. 1) inserted in the expression vector can be detected by DNA-DNA hybridization using probes comprising nucleotide sequences that are homologous to the TGF-β1/β2 coding sequence (SEQ ID No. 1) substantially as shown in FIG. 1, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the TGF-β1/β2 coding sequence (SEQ ID No. 1) is inserted within a marker gene sequence of the vector, recombinants containing the TGF-β1/β2 coding sequence (SEQ ID No. 1) can be identified by the absence of the marker gene function. Alternatively, a marker gene can be placed in tandem with the TGF-β1/β2 sequence (SEQ ID No. 1) under the control of the same or different promoter used to control the expression of the TGF-β1/β2 coding sequence (SEQ ID No. 1). Expression of the marker in response to induction or selection indicates expression of the TGF-β1/β2 coding sequence (SEQ ID No. 1).

In the third approach, transcriptional activity for the TGF-β1/β2 coding region (SEQ ID No. 1) can be assessed by hybridization assays. For example, polyadenylated RNA can be isolated and analyzed by Northern blot using a probe homologous to the TGF-β1/β2 coding sequence (SEQ ID No. 1) or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as immunoblotting, radioimmunoprecipitation, enzyme-linked immunoassays, and the like. The ultimate test of the success of the expression system, however, involves the detection of the biologically active TGF-β1/β2 gene product. Where the host cell secretes the gene product, the cell free media obtained from the cultured transfectant host cell may be assayed for TGF-β1/β2 activity. Where the gene product is not secreted, cell lysates may be assayed for such activity. In either case, biological assays such as the growth inhibition assay described herein or the like may be used.

Once a clone producing high levels of mature TGF-β1/β2 is identified, the clone may be expanded and the TGF-β1/β2 may be purified using techniques well known in the art. Such methods include immunoaffinity purification, chromatographic methods including high performance liquid chromatography, and the like.

5.4. IMPROVED METHOD FOR PRODUCING MATURE TGF-β1/β2

In a specific embodiment of the invention, the TGF-β1/β2 precursor may be modified by eliminating the amino acid cysteine at position 33 (CYS-33) of FIG. 1 (SEQ ID No. 2) and replacing it with serine. This modification may be introduced at the DNA level using site directed mutagenesis. COS cells transfected with plasmids encoding the TGF-β1 precursor gene so modified ultimately secrete between three and five times more mature TGF-β1 than do CHO cells expressing the unmodified precursor gene. It is believed that this modification prevents the formation of certain disulfide-linked precursor complexes in the transfected COS cells and therefore allows for the secretion of more mature TGF-β.

6. EXAMPLE: PRODUCTION OF TGF-β1/β2 BY EXPRESSION IN CHINESE HAMSTER OVARY CELLS

A recombinant plasmid encoding TGF-β1 precursor in which amino acids 9, 10, 11, 12, 13, 17, 19, 25 and 26 of the mature TGF-β1 sequence were replaced by the corresponding amino acids of the mature TGF-β2 sequence was constructed (SEQ ID No. 1). Specifically, amino acid 9 of mature TGF-β1 (serine) was replaced by arginine, amino acid number 10 (serine) was replaced by asparagine, amino acid number 11 (threonine) was replaced by valine, amino acid number 12 (glutamic acid) was replaced by glutamine, amino acid number 13 (lysine) was replaced by aspartic acid, amino acid number 17 (valine) was replaced by leucine, amino acid number 19 (glutamine) was replaced by proline, amino acid number 25 (arginine) was replaced by lysine and amino acid number 26 (lysine) was replaced by arginine. The construct was used to transfect CHO cells. Transfectants which produced and secreted a mature, bioactive, chimeric TGF-β1/β2 were isolated.

6.1. MATERIALS AND METHODS

6.1.1. DNA TRANSFECTIONS

Approximately 24 hours after seeding $10^6$ dhfr-deficient CHO cells onto 100 mm dishes, the cultures were transfected with 1 μg of NdeI linearized p5/dhfr plasmid and 19 μg of calf thymus DNA as carrier as a calcium phosphate precipitate (Wigler, M., et al., 1979, Proc. Natl. Acad. Sci. U.S.A. 76:1373–1376). Briefly, 20 μg of plasmid plus carrier DNA was added to 1 ml of 250 mM sterile $CaCl_2$. The DNA solution (1 ml) was added dropwise to a 1 ml portion of 2X HEPES solution (280 mM NaCl, 50 mM HEPES, 1.5 mM sodium phosphate, pH 7.1) while bubbling and the mixture was allowed to sit on ice for 30 minutes. The precipitate was then dispersed dropwise over the cells containing 10 ml of F12 media (Gibco). After incubation at 37° C. for 4 hours, the media was removed and replaced with 10 ml of F12 media containing 25% glycerol for 90 seconds at room temperature. Cells were rinsed once with 20 ml of F12 media and incubated in the nonselective F12 media (20 ml) for an additional 48 hours. Selection for dhfr expressing transfectants was accomplished by replacing the media with DMEM supplemented with 10% dialyzed FBS (Gibco) and 150 μg/ml L-proline. Colonies were observed after culturing the cells 10–14 days in the selection media.

6.1.2. SELECTION OF METHOTREXATE RESISTANT CELLS

Dihydrofolate reductase (dhfr) amplified cells were derived from the primary transfectants essentially as described (Gasser, C.S. and Schimke, R.T., 1986, J. Biol. Chem. 261:6938–6946). After expansion, $10^5$ cells were seeded onto 100 mm dishes and adapted to increasing concentrations of methotrexate (100 nM; 500 nM; 2,500 nM; 10,000 nM; 20,000 nM). The initial concentration of methotrexate was 100 nM. The plate containing visible colonies was trypsinized and adapted to that concentration of methotrexate for at least two additional 1:5 cell passages. Cells ($10^5$) were then seeded onto 100 mm dishes in the next highest concentration of methotrexate. The dish containing visible colonies was again trypsinized and adapted in the methotrexate containing medium. Cells were frozen back at various stages of amplification in media containing 40% FBS, 10% dimethyl sulfoxide and 50% DMEM. Methotrexate was not included in the freezing media.

6.1.3. GROWTH INHIBIT

Mink lung epithelial cells, Mv 1 Lu (Accession Number CCL-64, American Type Culture Collection), which are extremely sensitive to TGF-β were utilized for the growth inhibition assay. The assay was performed using the thymidine analog $5\alpha$-[$^{125}$I]-iodo-2'deoxyuridine ($^{125}$IdU) to assess DNA synthesis. One unit of activity was defined as the amount required to inhibit 50% incorporation of $^{125}$IdU compared to untreated CCL-64 cells.

To assay transfected cells for secretion of active TGF-β1/β2, serum free supernatants were collected from one 24 hour collection on confluent cultures of cells and dialyzed extensively against 0.2 M acetic acid. Samples were diluted into sterile complete culture medium for assays.

6.1.4. PEPTIDE SYNTHESIS AND PRODUCTION OF ANTIBODIES

Peptides were synthesized by solid phase techniques on a Beckman 990 instrument, and cleaved from the resin as previously described (Gentry, L.E., et al., 1983, J. Biol. Chem. 258:11219–11228; Gentry, L.E. and Lawton, A., 1986, Virology 152:421–431). Purification was accomplished by preparative high performance liquid chromatography. The composition of the peptides was confirmed by amino acid analysis.

Synthetic peptides were conjugated to bovine gamma-globulin through the cysteine residue. Coupling reactions were performed essentially as described (Gentry and Lawton, 1986, supra). The efficiencies of peptide conjugations ranged from 8 to 26 molecules of peptide covalently attached per molecule of gamma-globulin.

New Zealand white rabbits were primed at three to six sites by combined subcutaneous and intradermal inoculations with the peptide conjugates (100 μg equivalents of peptide) emulsified in Freunds complete adjuvant. Booster inoculations were administered at 2–3 week intervals. Bleedings were taken 7–14 days following the boosts.

Anti-peptide antibodies directed toward peptide sequences within the TGF-β1 molecule were generated in rabbits using synthetic peptides as immunogens (Gentry et al., 1987, Mol. Cell. Biol. 7:3418–3427). One of the antibodies (anti-TGF-β1$_{369-381}$) was directed toward epitopes present within the mature form of the TGF-β growth factor. The other two antibodies (anti-TGF-β1$_{81-94}$ and anti-TGF-β1$_{225-236}$) are precursor-specific and are directed toward peptide sequences (SEQ ID No. 2) present only within the precursor molecule of TGF-β1.

6.1.5. IMMUNOBLOTTING

Proteins were fractionated on 7.5%–17.5% gradient SDS-polyacrylamide gels and transferred to unmodified nitrocellulose (0.45 μm; Schleicher and Schuell) for 1 hour at 24 volts at 4° C. (Burnette, W.N., 1981, Anal. Biochem. 112:195–203). Excess binding capacity of the nitrocellulose was blocked by incubation with 2.5% BLOTTO (Johnson, D.A., et al., 1984, Gene Anal. Techn. 1:3–8) in phosphate-buffered saline (PBS) containing 0.2% NP-40. Rabbit anti-serum diluted 1:75 in 2.5% BLOTTO was incubated with the blocked nitrocellulose sheets for 2 hours at room temperature. After washing away excess antibody by five 5-minute washes in 2.5% BLOTTO, the nitrocellulose sheets were incubated with alkaline phosphatase-conjugated Protein A diluted 1:500 in 2.5% BLOTTO. Following a two hour incubation, the nitrocellulose sheets were washed 5 times in PBS (5 minute washes) containing 0.2% NP-40 and developed (Leary et al., 1983, Proc. Natl. Acad. Sci. U.S.A. 80:4045-4049).

6.1.6. CONSTRUCTION OF PLASMID PROGRAMMING THE SYNTHESIS OF TGF-β1/β2

The plasmid programming the synthesis of the chimeric TGF-β1/β2 protein, p5β/dhfr, was constructed as follows. pAcβTGF-β1, a baculovirus vector derived from pAc373 (Miyamoto et al., 1985, Cell. Biol. 5:2860-2865; Madisen et al., 1987, Virology 158:248-250), which contains the 1.4 Kb PstI-EcoRI coding sequence of TGF-β1 (Sharples et al., 1987, DNA 6:239-244) cloned into the PstI-EcoRI site of pAc611 (Miyamoto et al., 1985, Cell. Biol. 5:2860-2865; Madisen et al., 1987, Virology 158:248-250), was digested with BamHI and EcoRI and the 375 bp fragment of the TGF-β1 coding sequence was isolated (Fragment 1). pSV2-TGF (Gentry et al., 1987, Mol. Cell. Biol. 7:3418-3427) was digested with ApaI and EcoRI and the 3.5 Kb fragment was isolated (Fragment 2).

Complementary synthetic oligonucleotides having the sequences shown below were synthesized on an Applied Biosystems Oligonucleotide Synthesizer and purified from an acrylamide gel. Phosphates were added with T4 kinase and equimolar amounts of the kinased oligonucleotides were annealed. The annealed double stranded synthetic DNA was then ligated to fragments '1' and '2' described above. The ligation mixture was used to transform *E. coli* and 5βpSV2(Hpa⁻Eco⁺) was isolated.

```
5' - CAA CAT CTG CAA AGC TCC CGG CAC CGC CGA GCC

CTG GAC ACC AAC TAC TGC TTC AGA AAT GTG CAG

GAT AAT TGC TGC CTA CGT CCG CTT TAC ATT GAT

TTC AAG AGG GAT CTA GGG TGG AAA TG - 3'

5' - GAT CCA TTT CCA CCC TAG ATC CTT CTT GAA ATC

AAT GTA AGC GGA CGT AGG CAG CAA TTA ATC CTG

CAC ATT TCT GAA GCA GTA GTT GGT GTC AGG GGC

TCG GCG GTG CCG GGA GCT TTG CAG ATG TTG GGC C - 3'
```

5βpSV2(Hpa⁻Eco⁺) was digested with EcoRI, filled in with Klenow enzyme, digested with HindIII and the 1.4 Kb fragment containing the chimeric TGF-β1/β2 coding sequence (SEQ ID No.: 1) was isolated (Fragment 3). 5βpSV2 was constructed by ligating Fragment 3 into pSV2,neo which had previously been digested with HindIII and HpaI to eliminate the neo gene.

5βpSV2 was digested with EcoRI, filled in with Klenow enzyme, digested with NdeI and the 2.6 Kb NdeI-EcoRI (blunt) fragment was isolated and ligated to pSV2/dhfr (Gentry et al., 1987, Mol. Cell. Biol. 7:3718-3727) which had been digested with NdeI and PvuII. The ligation mixture was used to transform *E. coli* and p5β/dhfr was isolated. The nucleotide and deduced amino acid sequences of the chimeric TGF-β1/β2 molecule encoded by p5/dhfr are shown in FIG. 1 (SEQ ID No. 1, 2, 4).

6.2. EXPRESSION OF TGF-β1/β2 IN CHO CELLS p5β/dhfr was transfected into CHO cells and single clones were amplified with methotrexate as described in Section 6.1., supra. One such amplified clone, CHO-5β41,2.5, was chosen for further characterization.

CHO-5β41,2.5 cells were grown to confluence in 2.5 μM methotrexate. Media was replaced with serum free media and, after 24 hr, was collected and dialyzed for 48 hr against 0.2M acetic acid. Dialyzed, conditioned supernatants were assayed for bioactivity by inhibition of DNA synthesis of CCL-64 cells as described in Section 6.1.3., supra. CHO-5β41,2.5 cells secrete approximately 1 mg/L of bioactive chimeric TGF-β1/β2 (FIG. 2).

TGF-β related proteins secreted by these cells were analyzed by immunoblotting using anti-peptide antibodies directed against mature TGF-β1 as described in Section 6.1.5., supra FIG. 3 shows that CHO-5β41,2.5 cells secrete immunoreactive proteins migrating at 90 to 100 kilodaltons and at 24 kilodaltons when analyzed on SDS-PAGE under nonreducing conditions (FIG. 3, lane 1). The 24 kilodalton band represents the mature TGF-β1/β2 dimer and the 90 to 100 kilodalton protein probably represents mature TGF-β1/β2 disulfide-bonded to precursor sequences (Gentry et al., 1987, Mol. Cell. Biol. 7:3418-3427).

Under reducing conditions (FIG. 3, lane 2), the majority of the proteins migrate at 12 kilodaltons, representing the mature TGF-β1/β2 monomer. Note the lack of immunoreactive material in the 45 to 55 kilodalton range observed in a similar analysis of recombinant proteins expressed in CHO cells tranfected with plasmids encoding the simian TGF-β1 gene (Gentry et al., 1987, Mol. Cell. Biol. 7:3418-3427) suggesting that chimeric TGF-β1/β2 is proteolytically processed more efficiently than its parent molecule TGF-β1. In addition, CHO-5β41,2.5 cells secrete about 2.5 times more bioactive mature product than do CHO cells expressing TGF-β1 (Gentry et al., 1987, supra). Although the basis for these observations is presently unknown, the secondary structure of the chimeric TGF-β1/β2 precursor may significantly differ from the secondary structure of TGF-β1, which secondary structure renders the chimeric TGF-β1/β2 subject to molecular processing events of a different intensity or nature. For example, the TGF-β1/β2 precursor may be a more favorable substrate for the factors involved in TGF-β processing. Alternatively, the secondary structural characteristics of TGF-β1/β2 may allow it to interact with other processing factors or pathways not as accessible to TGF-β1.

7. EXAMPLE: GROWTH MODULATION OF VASCULAR ENDOTHELIAL CELLS BY HYBRID TGF-5β

Using three distinct bioassays which previously indicated that differential responses are induced by TGF-β1 and TGF-β2 (Merwin et al., 1991, Am. J. Path. 138(1):37-51), the biological effects induced by recombinant hybrid TGF-1/β2 (TGF-5β) on the proliferation, migration and angiogenesis of large vessel endothelial, smooth muscle and microvascular endothelial cells were examined.

7.1. MATERIALS AND METHODS

7.1.1. CELL CULTURE

Bovine aortic smooth muscle cells (BASMCs) were grown from explants of bovine aorta in complete DME supplemented with 10% FCS as described in Kocher and Madri, 1989, In Vitro Cell. & Dev. Biol. 25:424-34. After several days in culture, BASMCs migrate out from the medial explants. Following the development of confluency, the cells were trypsinized, passaged and utilized in the growth inhibitory assays described, infra. These α-smooth muscle, actin positive cells formed the hill-and-valley pattern typical of cultured smooth muscle cells and were used between passage 2 and 5.

Capillary endothelial cells were isolated and cultured from rat epididymal fat pads as described in Madri and Williams, 1983, J. Cell Biol. 97:153-65, and are hereinafter termed "RFCs". Bovine calf aortic endothelial cells (BAECs) were isolated and cultured as described in Madri and Furthmayr, 1980, Hum. Path. 11:353-66. Three-dimensional RFC cultures were composed of acid soluble calf dermis collagen type I and prepared using the method of Madri et al., 1988, J. Cell Biol. 106:1375-84. To address the possibility of differences due to the use of two species, proliferative, migratory and angiogenic studies were also performed using bovine adrenal cortex microvascular endothelial cells; the results were equivalent to those obtained with RFCs.

7.1.2. TGF-β FACTORS

Recombinant hybrid TGF-β1/β2 was produced as described in Section 6, et seq, supra. TGF-β1 and TGF-β2 were prepared, respectively, as described in Assoian et al., 1983, J. Biol. Chem. 258:7155-60, and in Cheifetz et al., 1987, Cell 48:409-15, and were obtained from Drs. A. Roberts and M. Sporn at the Laboratory of Chemoprevention, National Cancer Institute, Bethesda, Md.

7.1.3. MATRIX COMPONENTS

Tissue culture dishes and flasks were coated with purified bovine type I collagen (Madri and Furthmayr, 1980, Hum. Path. 11:353-66) at a concentration of 12.5 μg/ml.

7.1.4. PROLIFERATION INHIBITION ASSAY

Collagen type I-coated dishes were washed in PBS before the addition of cell suspensions ($1.4 \times 10^4$ cells/dish). After 6 h, the "initial"0 number of cells on the substrate was determined. At this time point, fresh medium with or without TGF-βs was added to the cultures. Medium and TGF-βs were replaced once again on day 3. Cell numbers were determined by lifting the cells off the culture dishes with trypsin/EDTA and counting quadruplicate samples using a Coulter counter (Coulter Electronics, Inc., Hialeah, Fla.). The mean number of cells per dish for each TGF-β addition was then calculated.

7.1.5. CELL MIGRATION ASSAYS

Stimulus for cell migration was accomplished by releasing confluent cultures from contact inhibition using a stainless steel "fence" device as previously described (Pratt et al., 1984, Am. J. Path. 117:349-54). Once confluency had been achieved in the center wells of the fences (~6 h), migration was induced by removing the fences, and cells were thereafter observed migrating outward in a radial fashion. Cultures were fed once again on day 3 with control or TGF-β-supplemented media. After 6 days, the cultures were washed with PBS, fixed with 10% neutral buffered formalin and stained with Harris hematoxylin. Net increase in surface area covered was assessed using an overhead projector, and areas were calculated utilizing a computerized graphics tablet and "MacMeasure" software (Yale Shareware, Yale Univeristy, New Haven, Conn.).

7.2. RESULTS

The majority of published reports indicate that the TGF-β1 and TGF-β2 isoforms are equipotent in vitro. However, recent reports indicate that these isoforms are not functionally interchangeable, since they elicit dissimilar effects and exhibit different spatial and temporal localizations (See, for example, Ohto et al., 1987, Nature 329:539-41; Rosa et al., 1988, Science 239:783-85; and Danielpour et al., 1989, J. Cell Physiol. 138:79-86). TGF-β1 is reportedly more effective than TGF-β2 in inhibiting DNA synthesis in endothelial cells (Jennings, et al., 1988, J. Cell. Physiol. 137:167-72).

A recent report establishes that TGF-β1 and TGF-β2 isoforms elicit differential responses in proliferation assays using three vascular cell types (Merwin et al., 1991, Am J. Path. 138(1):37-51). Therefore, investigating the effects of TGF-5β on endothelial cells seemed ideal for determining whether the TGF-β1/TGF-β2 hybrid (TGF-5β) would evoke responses similar to TGF-β1 or to TGF-β2. The results indicated that TGF-5β mimicked TGF-β1 in all three proliferation assays examined, while TGF-β2 displayed unique properties.

Both TGF-β1 and TGF-5β inhibited BAEC proliferation by more than 70% (+/−1.5%) at the optimum concentration of 0.5 ng/ml (FIG. 4A). In contrast, TGF-β2 was only able to evoke inhibition of about 20% (+/−2.5%). When using BASMCs, all three growth factors exhibited similar inhibitory activities (FIG. 4B). Microvascular endothelial cells were growth inhibited as much as 70% (+/−4.0%) by both TGF-β1 and TGF-5at concentrations of 0.5 ng/ml (FIG. 4C). At equivalent concentration, however, TGF-β2 was only able to mount a 37% (+/−8%) inhibition; however, with a 10-fold increase in concentration, TGF-β2 was able to evoke a similar response.

Similarly, hybrid TGF-5β exerted a cell migration response equivalent to that induced by TGF-β1. The results presented in FIG. 5 show that BAECs are inhibited by both TGF-5β and TGF-β1, while BASMCs are growth-stimulated by both factors. In contrast, TGF-β2 had no effect on the migration of either cell type.

The above results may help to explain vascular response to injury. Upon denudation (i.e., following angioplasty) of the endothelial barrier, platelets adhere and aggregate to the newly exposed subendothelial extracellular matrix and release a variety of molecules. In this regard, one of the major factors released by platelets is TGF-β1. With a marked increase in the local concentration of TGF-β1, endothelial cells may be inhibited from migrating to affect a rapid re-endothelialization of the injury while at the same time, smooth muscle cell migration toward an increased factor gradient may be stimulated, thereby establishing an ideal opportunity for perpetuating the expansion of the medial compartment of the vessel wall and continued occulsion of the vascular lumen.

While angiogenesis is an important and necessary response during embryogenesis and tissue repair, it is an undesirable phenomenon in the context of solid tumor growth. Therefore, understanding the enhancement of neovascularization is of paramount concern. To investigate the TGF-β-induced angiogenic response in microvascular endothelial cells, RFCs were grown in three-dimensional collagen cultures for 4 days, either in the presence or absence of TGF-β isoforms. All three isoforms were able to stimulate RFCs to mount a neovascularization response. This endothelial "activation" was previously defined by extensive EM analysis (Merwin et al., 1990, J. Cell. Physiol. 142:117–29) which revealed the formation of branching tubular structures, cell-cell junctional complexes, metabolic stimulation (increased numbers of ribosomes and engorged ER), cellular polarity, deposition and organization of extracellular matrix proteins and lumen formation.

Figure 6A:
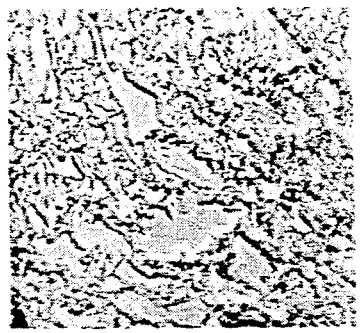
Figure 6B:
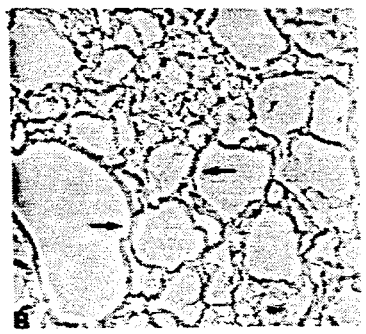
Figure 6C:
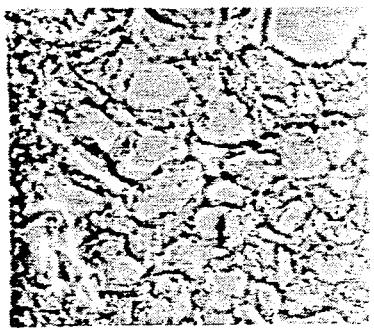
Figure 6D:
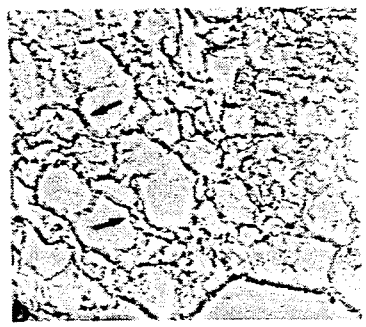
Figure 6E:
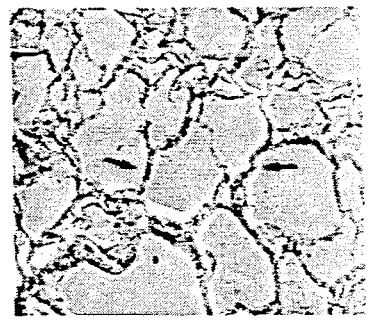
Figure 6F:

FIG. 6A shows control cultures with no exogenous growth factor. Cells remain independent of one another and lack tubular structures, while treatment with TGF-β1 (FIG. 6B) reveals complex, tube-like formations. TGF-β2 (FIG. 6C) was able to initiate a modest angiogenic response. However, as with RFC proliferation studies, an increase in TGF-β2 concentration from 0.5 to 5.0 ng/ml was necessary for the establishment of complex tubular structures. TGF-5β mimicked TGF-β1, with tube formation initiated with as little as 0.05 ng/ml (FIG. 6D), and optimal neovascularization achieved at a concentration of 0.5 ng/ml (FIG. 6E). A slight inhibition of the angiogenic response was noted at the highest concentration used, 5.0 ng/ml (FIG. 6F).

In summary, TGF-5β mimics TGF-β1 in inhibiting proliferation of low density monolayer micro and large vessel endothelial cell cultures by about 70% and by about 45% on BASMCs. In contrast, an equivalent concentration of TGF-β2 is ineffective with BAECs and equivalent on BASMCs. Moreover, a 10-fold increase in TGF-β2 concentration is required to elicit a similar response with RFCs. When using a culture which begins with a tight, confluent monolayer, response induced by the isoforms differ. In particular, both TGF-β1 and TGF-β2 induce equivalent levels of BASMC migration enhancement and BAEC migration inhibition, while TGF-β2 does not influence the migration of either cell type. Finally, in microvascular endothelial cells which respond to injury in vivo by neovascularization, all three TGF-βs were able to stimulate angiogenesis in vitro. However, a 10-fold increase in TGF-β2 concentration was necessary to match the level of response induced by TGF-β1 and TGF-5β.

8. DEPOSIT OF MICROORGANISMS

The following transfectant has been deposited on Jan. 11, 1989 with the American Type Culture Collection, 12301 Parklawn Drive, Rockville, Md., and has been assigned the listed accesion number.

| Transfectant | Plasmid | Accession No. |
| --- | --- | --- |
| CHO-5β41,2.5 CL 5 | p5β/dhfr | CRL 9959 |

The present invention is not to be limited in scope by the cell line deposited or the embodiments disclosed herein which are intended as single illustrations of one aspect of the invention and any which are functionally equivalent are within the scope of the invention. Indeed, various modifications of the invention, in addition to those shown and described herein, will become apparent to those skilled in the art from the foregoing description. Such modifications are intended to fall within the scope of the appended claims.

It is also to be understood that all base pair and amino acid residue numbers and sizes given for nucleotides and peptides are approximate and used for the purposes of description.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1560 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 261..1430

( x i ) SEQUENCE DESCRIPTION: SEQ ID NO:1:

AGGGGATCTG TGGCAGGTCG GAGAAAGATC CGTCTCCTGG TACCAGATCT CGCCCATCTA    60

-continued

```
GGTTATTTCC GTGGGATACT GAGACACCCC CGGTCCAAGC CTCCCCTCCA CCACTGCGCC      120

CTTCTCCCGT AGGACCTCAA CTTTCCCTCG AGGCCCTCCT ACCTTTTCCC GGGGGACCCC      180

CAGCCCCTGC AGGGCGGGG CCTCCCCACC AAACTAGCCC TGTTCGCGCT CTCGGCAGTG       240

CCGGGGGGCG CCGCCTCCCC ATG CCG CCC TCC GGG CTG CGG CTG CTG CCG          290
                       Met Pro Pro Ser Gly Leu Arg Leu Leu Pro
                         1           5                      10

CTG CTG CTA CCG CTG CTG TGG CTA CTG GTG CTG ACG CCT AGC CGG CCG        338
Leu Leu Leu Pro Leu Leu Trp Leu Leu Val Leu Thr Pro Ser Arg Pro
             15                  20                      25

GCC GCA GGA CTA TCC ACC TGC AAG ACT ATC GAC ATG GAG CTG GTG AAG        386
Ala Ala Gly Leu Ser Thr Cys Lys Thr Ile Asp Met Glu Leu Val Lys
         30              35                      40

CGG AAG CGC ATC GAG ACC ATC CGC GGC CAG ATC CTG TCC AAG CTG CGG        434
Arg Lys Arg Ile Glu Thr Ile Arg Gly Gln Ile Leu Ser Lys Leu Arg
     45              50                      55

CTC GCC AGC CCC CCG AGC CAG GGG GAG GTG CCG CCC GGC CCG CTG CCC        482
Leu Ala Ser Pro Pro Ser Gln Gly Glu Val Pro Pro Gly Pro Leu Pro
 60              65                      70

GAG GCC GTG CTC GCC CTG TAC AAC AGC ACC CGC GAC CGG GTG GCC GGG        530
Glu Ala Val Leu Ala Leu Tyr Asn Ser Thr Arg Asp Arg Val Ala Gly
 75              80                      85                      90

GAG AGT GCG GAG CCG GAG CCC GAA CCG GAG GCC GAC TAC TAC GCC AAG        578
Glu Ser Ala Glu Pro Glu Pro Glu Pro Glu Ala Asp Tyr Tyr Ala Lys
             95                      100                     105

GAG GTC ACC CGC GTG CTA ATG GTG GAA ACC CAC AAC GAA ATC TAT GAC        626
Glu Val Thr Arg Val Leu Met Val Glu Thr His Asn Glu Ile Tyr Asp
             110                     115                     120

AAG TTC AAG CAG AGC ACA CAC AGC ATA TAT ATG TTC TTC AAC ACA TCA        674
Lys Phe Lys Gln Ser Thr His Ser Ile Tyr Met Phe Phe Asn Thr Ser
         125                     130                     135

GAG CTC CGA GAA GCA GTA CCT GAA CCT GTG TTG CTC TCC CGG GCA GAG        722
Glu Leu Arg Glu Ala Val Pro Glu Pro Val Leu Leu Ser Arg Ala Glu
     140                     145                     150

CTG CGT CTG CTG AGG CTC AAG TTA AAA GTC GAG CAG CAT GTG GAG CTG        770
Leu Arg Leu Leu Arg Leu Lys Leu Lys Val Glu Gln His Val Glu Leu
155                     160                     165                 170

TAC CAG AAA TAC AGC AAC AAT TCC TGG CGA TAC CTC AGC AAC CGG CTG        818
Tyr Gln Lys Tyr Ser Asn Asn Ser Trp Arg Tyr Leu Ser Asn Arg Leu
                 175                     180                     185

CTG GCG CCC AGC AAC TCG CCG GAG TGG TTG TCT TTT GAT GTC ACC GGA        866
Leu Ala Pro Ser Asn Ser Pro Glu Trp Leu Ser Phe Asp Val Thr Gly
             190                     195                     200

GTT GTG CGG CAG TGG TTG AGC CGC GGA GGG GAA ATT GAG GGC TTT CGC        914
Val Val Arg Gln Trp Leu Ser Arg Gly Gly Glu Ile Glu Gly Phe Arg
205                     210                     215

CTT AGC GCC CAC TGC TCC TGT GAC AGC AAA GAT AAC ACA CTG CAA GTG        962
Leu Ser Ala His Cys Ser Cys Asp Ser Lys Asp Asn Thr Leu Gln Val
         220                     225                     230

GAC ATC AAC GGG TTC ACT ACC GGC CGC CGA GGT GAC CTG GCC ACA ATT        1010
Asp Ile Asn Gly Phe Thr Thr Gly Arg Arg Gly Asp Leu Ala Thr Ile
235                     240                     245                 250

CAT GGC ATG AAC CGG CCT TTC CTG CTT CTC ATG GCC ACC CCG CTG GAG        1058
His Gly Met Asn Arg Pro Phe Leu Leu Leu Met Ala Thr Pro Leu Glu
                 255                     260                     265

AGG GCC CAA CAT CTG CAA AGC TCC CGG CAC CGC CGA GCC CTG GAC ACC        1106
Arg Ala Gln His Leu Gln Ser Ser Arg His Arg Arg Ala Leu Asp Thr
             270                     275                     280

AAC TAC TGC TTC AGC TCC ACG GAG AAG AAC TGC TGC GTG CGG CAG CTG        1154
Asn Tyr Cys Phe Ser Ser Thr Glu Lys Asn Cys Cys Val Arg Gln Leu
```

|  |  |  |  |  |  |  |  |  |  |  |  |  |  |  |  |
|---|---|---|---|---|---|---|---|---|---|---|---|---|---|---|---|
|  | 285 |  |  |  | 290 |  |  |  |  |  | 295 |  |  |  |  |
| TAT | ATT | GAC | TTC | CGC | AAG | GAC | CTC | GGC | TGG | AAG | TGG | ATC | CAC | GAG | CCC |
| Tyr | Ile | Asp | Phe | Arg | Lys | Asp | Leu | Gly | Trp | Lys | Trp | Ile | His | Glu | Pro |
|  | 300 |  |  |  | 305 |  |  |  |  |  | 310 |  |  |  |  |

1202

```
AAG GGC TAC CAT GCC AAC TTC TGC CTG GGG CCC TGT CCC TAC ATT TGG    1250
Lys Gly Tyr His Ala Asn Phe Cys Leu Gly Pro Cys Pro Tyr Ile Trp
315             320             325             330

AGC CTG GAC ACG CAG TAC AGC AAG GTC CTG GCC CTG TAC AAC CAG CAT    1298
Ser Leu Asp Thr Gln Tyr Ser Lys Val Leu Ala Leu Tyr Asn Gln His
            335             340             345

AAC CCG GGC GCC TCG GCG GCG CCG TGC TGC GTG CCG CAG GCG CTG GAG    1346
Asn Pro Gly Ala Ser Ala Ala Pro Cys Cys Val Pro Gln Ala Leu Glu
        350             355             360

CCA CTG CCC ATC GTG TAC TAC GTG GGC CGC AAG CCC AAG GTG GAG CAG    1394
Pro Leu Pro Ile Val Tyr Tyr Val Gly Arg Lys Pro Lys Val Glu Gln
        365             370             375

CTG TCC AAC ATG ATC GTG CGC TCC TGC AAA TGC AGC TGAGGCCCCG         1440
Leu Ser Asn Met Ile Val Arg Ser Cys Lys Cys Ser
        380             385             390

CCCCGCCCCG CCCCACCCCG GCAGGCCCGG CCCCGCCCCA CCCCACCCCC GCTGTCTTGC  1500

CCTTGGGGGC TGTATTTAAG GACACCCGTG CCCCAAGCCC ACCTGGGGCC CCATTAAAGA  1560
```

( 2 ) INFORMATION FOR SEQ ID NO:2:

( i ) SEQUENCE CHARACTERISTICS:
        ( A ) LENGTH: 390 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Pro Ser Gly Leu Arg Leu Leu Pro Leu Leu Leu Pro Leu Leu
 1               5                  10                  15

Trp Leu Leu Val Leu Thr Pro Ser Arg Pro Ala Ala Gly Leu Ser Thr
            20                  25                  30

Cys Lys Thr Ile Asp Met Glu Leu Val Lys Arg Lys Arg Ile Glu Thr
        35                  40                  45

Ile Arg Gly Gln Ile Leu Ser Lys Leu Arg Leu Ala Ser Pro Pro Ser
 50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
            85                  90                  95

Pro Glu Pro Glu Ala Asp Tyr Tyr Ala Lys Glu Val Thr Arg Val Leu
        100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asn Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
```

|  |  |  | 210 |  |  |  |  | 215 |  |  |  | 220 |  |
|---|---|---|---|---|---|---|---|---|---|---|---|---|---|
| Cys 225 | Asp | Ser | Lys | Asp | Asn 230 | Thr | Leu | Gln | Val | Asp 235 | Ile | Asn | Gly | Phe | Thr 240 |
| Thr | Gly | Arg | Arg | Gly 245 | Asp | Leu | Ala | Thr | Ile 250 | His | Gly | Met | Asn | Arg 255 | Pro |
| Phe | Leu | Leu | Leu 260 | Met | Ala | Thr | Pro | Leu 265 | Glu | Arg | Ala | Gln 270 | His | Leu | Gln |
| Ser | Ser | Arg 275 | His | Arg | Arg | Ala | Leu 280 | Asp | Thr | Asn | Tyr | Cys 285 | Phe | Ser | Ser |
| Thr | Glu 290 | Lys | Asn | Cys | Cys 295 | Val | Arg | Gln | Leu | Tyr | Ile 300 | Asp | Phe | Arg | Lys |
| Asp 305 | Leu | Gly | Trp | Lys | Trp 310 | Ile | His | Glu | Pro | Lys 315 | Gly | Tyr | His | Ala | Asn 320 |
| Phe | Cys | Leu | Gly | Pro 325 | Cys | Pro | Tyr | Ile | Trp 330 | Ser | Leu | Asp | Thr | Gln 335 | Tyr |
| Ser | Lys | Val | Leu 340 | Ala | Leu | Tyr | Asn | Gln 345 | His | Asn | Pro | Gly | Ala 350 | Ser | Ala |
| Ala | Pro | Cys 355 | Cys | Val | Pro | Gln | Ala 360 | Leu | Glu | Pro | Leu | Pro 365 | Ile | Val | Tyr |
| Tyr | Val 370 | Gly | Arg | Lys | Pro | Lys 375 | Val | Glu | Gln | Leu | Ser | Asn 380 | Met | Ile | Val |
| Arg 385 | Ser | Cys | Lys | Cys | Ser 390 |

(2) INFORMATION FOR SEQ ID NO:3:

(i) SEQUENCE CHARACTERISTICS:
        (A) LENGTH: 1569 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CTCCGACCTG CCACAGATCC CCTATTCAAG ACCACCCACC TTCTGGTACC AGATCGCGCC      60
CATCTAGGTT ATTTCCGTGG GATACTGAGA CACCCCGGT CCAAGCCTCC CCTCCACCAC      120
TGCGCCCTTC TCCCGTAGGG CCTCGACTTT CCCTCGAGGC CCTCCTACCT TTTGCCGGGA     180
GACCCCCAGC CCCTGCAGGG GCGGGGCCTC CCCACCACAC CAGCCCTGTT CGCGCTCTCG     240
GCAGTGCCGG GGGGCGCCGC CTCCCCATGC CGCCCTCCGG GCTGCGGCTG CTGCCGCTGC     300
TGCTACCGCT GCTGTGGCTA CTGGTGCTGA CGCCTGGCCC GCCGGCCGCA GGACTATCCA     360
CCTGCAAGAC TATCGACATG GAGCTGGTGA AGCGGAAGCG CATCGAGGCC ATCCGCGGCC     420
AGATCCTGTC CAAGCTGCGG CTCGCCAGCC CCCGAGCCA GGGGGAGGTG CCGCCCGGCC      480
CGCTGCCCGA GGCCGTGCTC GCCCTGTACA ACAGCACCCG CGACCGGGTG GCCGGGGAGA     540
GTGCAGAACC GGAGCCCGAG CCTGAGGCCG ACTACTACGC CAAGGAGGTC ACCCGCGTGC     600
TAATGGTGGA AACCCACAAC GAAATCTATG ACAAGTTCAA GCAGAGTACA CACAGCATAT     660
ATATGTTCTT CAACACATCA GAGCTCCGAG AAGCGGTACC TGAACCCGTG TTGCTCTCCC     720
GGGCAGAGCT GCGTCTGCTG AGGAGGCTCA AGTTAAAAGT CGAGCAGCAC GTGGAGCTGT     780
ACCAGAAATA CAGCAACAAT TCCTGGCGAT ACCTCAGCAA CCGGCTGCTG GCACCCAGCG     840
ACTCGCCAGA GTGGTTATCT TTTGATGTCA CCGGAGTTGT GCGGCAGTGG TTGAGCCGTG     900
GAGGGGAAAT TGAGGGCTTT CGCCTTAGCG CCCACTGCTC CTGTGACAGC AGGGATAACA     960
CACTGCAAGT GGACATCAAC GGGTTCACTA CCGGCCGCCG AGGTGACCTG GCCACAATTC    1020
```

| | | | | | |
|---|---|---|---|---|---|
| ATGGCATGAA | CCGGCCTTTC | CTGCTTCTCA | TGGCCACCCC | GCTGGAGAGG | GCCCAGCATC | 1080
| TGCAAAGCTC | CCGGCACCGC | CGAGCCCTGG | ACACCAACTA | TTGCTTCAGA | AATGTGCAGG | 1140
| ATAATTGCTG | CCTACGTCCG | CTTTACATTG | ATTTCAAGAG | GGATCTAGGC | TGGAAGTGGA | 1200
| TCCACGAGCC | CAAGGGCTAC | CATGCCAACT | TCTGCCTCGG | GCCCTGCCCC | TACATTTGGA | 1260
| GCCTGGACAC | GCAGTACAGC | AAGGTCCTGG | CCCTGTACAA | CCAGCATAAC | CCGGGCGCCT | 1320
| CGGCGGCGCC | GTGCTGCGTG | CCGCAGGCGC | TGGAGCCGCT | GCCCATCGTG | TACTACGTGG | 1380
| GCCGCAAGCC | CAAGGTGGAG | CAGCTGTCCA | ACATGATCGT | GCGCTCCTGC | AAGTGCAGCT | 1440
| GAGGTCCCGC | CCCGCCCCGC | CCCGCCCCGG | CAGGCCCGGC | CCCACCCCGC | CCCGCCCCCG | 1500
| CTGCCTTGCC | CATGGGGGCT | GTATTTAAGG | ACACCCGTGC | CCCAAGCCCA | CCTGGGGCCC | 1560
| CATTAAAGA | | | | | | 1569

What is claimed is:

1. A method of inhibiting the proliferation of vascular endothelial cells comprising contacting the cells with chimeric transforming growth factor TGF-5β consisting of amino acids 279 to 390 as given in FIG. 1.

2. A method of inducing smooth muscle cell migration comprising contacting the cell with chimeric transforming growth factor TGF-5β consisting of amino acids 279 to 390 as given in FIG. 1.

* * * * *